US011559510B2

(12) United States Patent
Kelly et al.

(10) Patent No.: US 11,559,510 B2
(45) Date of Patent: Jan. 24, 2023

(54) ISOFLAVONOID COMPOSITION WITH IMPROVED PHARMACOKINETICS

(71) Applicant: NOXOPHARM LIMITED, Turramurra (AU)

(72) Inventors: Graham Kelly, Turramurra (AU); Kate Porter, Turramurra (AU)

(73) Assignee: NOXOPHARM LIMITED, Turramurra (AU)

( * ) Notice: Subject to any disclaimer, the term of this patent is extended or adjusted under 35 U.S.C. 154(b) by 417 days.

(21) Appl. No.: 16/091,716

(22) PCT Filed: Apr. 6, 2017

(86) PCT No.: PCT/AU2017/050301
§ 371 (c)(1),
(2) Date: Oct. 5, 2018

(87) PCT Pub. No.: WO2017/173498
PCT Pub. Date: Oct. 12, 2017

(65) Prior Publication Data
US 2019/0117618 A1    Apr. 25, 2019

Related U.S. Application Data

(60) Provisional application No. 62/318,946, filed on Apr. 6, 2016, provisional application No. 62/480,692, filed on Apr. 3, 2017.

(30) Foreign Application Priority Data

Jul. 28, 2016  (AU) .................. PCT/AU2016/050674

(51) Int. Cl.
*A61K 31/352*    (2006.01)
*A61K 9/00*    (2006.01)
*A61K 9/02*    (2006.01)
*A61K 31/353*    (2006.01)
*A61P 35/00*    (2006.01)

(52) U.S. Cl.
CPC .......... *A61K 31/352* (2013.01); *A61K 9/0031* (2013.01); *A61K 9/02* (2013.01); *A61K 31/353* (2013.01); *A61P 35/00* (2018.01)

(58) Field of Classification Search
CPC .. A61K 31/352; A61K 31/353; A61K 9/0031; A61K 9/02; A61P 35/00
See application file for complete search history.

(56) References Cited

U.S. PATENT DOCUMENTS

| 4,837,214 A * | 6/1989 | Tanaka ................ A61K 9/02 |
| | | 514/179 |
| 7,488,494 B2 | 2/2009 | Heaton et al. |
| 7,601,855 B2 | 10/2009 | Heaton et al. |
| 2004/0152761 A1 | 8/2004 | Heaton et al. |
| 2005/0049424 A1 | 3/2005 | Kelly et al. |
| 2005/0154452 A1* | 7/2005 | Hezi-Yamit ............ A61L 31/16 |
| | | 623/1.42 |
| 2006/0100238 A1 | 5/2006 | Kelly et al. |
| 2007/0036834 A1 | 2/2007 | Pauletti et al. |
| 2007/0196381 A1 | 8/2007 | Holt |
| 2009/0028964 A1 | 1/2009 | Muni et al. |
| 2009/0104235 A1 | 4/2009 | Heinrich |
| 2009/0233999 A1 | 9/2009 | Heaton et al. |
| 2010/0152284 A1* | 6/2010 | Brown .................... A61P 35/00 |
| | | 514/456 |
| 2012/0039917 A1 | 2/2012 | Husband et al. |
| 2016/0340329 A1 | 11/2016 | Heaton et al. |
| 2019/0117620 A1 | 4/2019 | Kelly |
| 2019/0160004 A1 | 5/2019 | Kelly |

FOREIGN PATENT DOCUMENTS

| WO | WO 1998/008503 | 3/1998 |
| WO | WO 2000/066576 | 11/2000 |
| WO | WO 2003/035635 | 5/2003 |
| WO | WO 2003/086386 | 10/2003 |
| WO | WO 2004/009035 | 1/2004 |
| WO | WO 2004/030662 | 4/2004 |
| WO | WO 2005/027842 | 3/2005 |
| WO | WO 2005/049008 | 6/2005 |
| WO | WO 2006/032086 | 3/2006 |
| WO | WO 2006/108212 | 10/2006 |
| WO | WO 2007/035515 | 3/2007 |
| WO | WO 2009/003229 | 1/2009 |
| WO | WO 2010/022467 | 3/2010 |
| WO | WO 2010/054438 | 5/2010 |
| WO | WO 2011/121418 | 10/2011 |
| WO | WO 2013/056217 | 4/2013 |
| WO | WO 2014/160130 | 10/2014 |

(Continued)

OTHER PUBLICATIONS

Herst_Phenoxodiol_PMET_in_tumour_cell_Biochem._Pharm._Aug p. 1587 2007 (Year: 2007).*
Souza NV06 (Phenoxodiol) Cancer Chemother Pharmacol, p. 427 (Year: 2006).*
GVS Advantages of Suppositories p. 1, December (Year: 2016).*
Aguero et al., "Phenoxodiol inhibits growth of metastatic prostate cancer cells," The Prostate, 70(11):1211-1221, 2010.
Ahmad et al., "Perspectives on the Role of Isoflavones in Prostate Cancer", The AAPS Journal, vol. 15, No. 4, Jul. 4, 2013 (Jul. 4, 2013), pp. 991-1000, XP55626811, DOI: 10.1208/s12248-013-9507-1 pp. 994-995.
Ahmad et al., "Soy isoflavones in conjunction with radiation therapy in patients with prostate cancer," Nutrition and Cancer England 2010, Taylor & Francis, US, vol. 62, No. 7, Jan. 1, 2010 (Jan. 1, 2010), pp. 996-1000.

(Continued)

*Primary Examiner* — Matthew P Coughlin
*Assistant Examiner* — Thurman Wheeler
(74) *Attorney, Agent, or Firm* — ParkerHighlander, PLLC

(57) ABSTRACT

A method for providing a steady state plasma concentration of about 20-400 ng/ml of isoflavonoid compounds comprising the steps of a first rectal administration of the compound in a lipophilic suppository base followed by further rectal administrations no earlier than 4, 8 or 16 hours after the previous rectal administration.

26 Claims, 1 Drawing Sheet

(56) References Cited

FOREIGN PATENT DOCUMENTS

| WO | WO 2015/069562 | 5/2015 | | |
|---|---|---|---|---|
| WO | WO 2016/024231 | 2/2016 | | |
| WO | WO 2016/028672 | 2/2016 | | |
| WO | WO-2016192680 A1 | * 12/2016 | ........... | A61K 9/2072 |
| WO | WO 2017/025918 | 2/2017 | | |
| WO | WO 2017/079746 | 5/2017 | | |
| WO | WO 2017/173498 | 10/2017 | | |
| WO | WO 2017/181242 | 10/2017 | | |
| WO | WO 2018/111902 | 6/2018 | | |
| WO | WO 2019/240871 | 12/2019 | | |
| WO | WO 2019/240872 | 12/2019 | | |
| WO | WO 2020/051644 | 3/2020 | | |

OTHER PUBLICATIONS

Anonymous, "Brain Cancer Study Commences," Feb. 1, 2017 (Feb. 1, 2017), pp. 1-3, XP55639769, Sydney, Australia Retrieved from the Internet: URL:https://www.noxopharm.com/site/PDF/1147O/BrainCancerStudyCommences [retrieved on Nov. 6, 2019].

Anonymous, "Idronoxil suppository NOX66", National Cancer Institute Drug Dictionary, XP009514254. Retrieved from the Internet <URL:https://www.cancer.gov/publications/dictionaries/cancer-drug/def/idronoxil-suppository-nox66> on May 2, 2017.

Cho et al., (2016) "Does Radiotherapy for the Primary Tumor Benefit Prostate Cancer Patients with Distant Metastasis at Initial Diagnosis?" Plos One, 11(1) e0147191. doi:10.1371/journal.pone.0147191.

Cremer Health, "Witepsol," Retrieved on Sep. 27, 2019. Retrieved from the internet <URL: https://www.pharmacompass.com/pAssets/pdf/edqm/application/witepsol.pdf>; pp. 1-44. (Year: 2019).

Database WPI Week 201204 Thomson Scientific, London, GB; An 2011-B25102 & KR 2011 0004525 A (Univ Dong Eui Ind Academic Coop Found), © WPI / 2017 Clarivate Analytics.

Gruca et al., "Synthetic genistein glycosides inhibiting EGFR phosphorylation enhance the effect of radiation in HCT 116 colon cancer cells," Molecules, 19(11): 18558-18573, 2014.

Kim et al., "Genistein decreases cellular redox potential, partially suppresses cell growth in HL-60 leukemia cells and sensitizes cells toy-radiation-induced cell death," Molecular Medicine Reports, 10(6):2786-2792, 2014.

Lock et al., (2015) "Abscopal Effects: Case Report and Emerging Opportunities," Cureus, DOI: 10.7759/cureus.344.

Ludgate, "Optimizing cancer treatments to induce an acute immune response: radiation Abscopal effects, PAMPs, and DAMPs," Clinical Cancer Research, 18(17):4522-4525, 2012.

McPherson et al., "Enhancement of the activity of phenoxodiol by cisplatin in prostate cancer cells," British Journal of Cancer, 100(4):649-655, 2009.

Noxopharm Limited, "Phase Ia/Ib and Potential Phase IIa Study of the Safety and Pharmacokinetics of NOX66 Both as a Monotherapy and in Combination with Carboplatin in Patients with Refractory Solid Tumours," ClinicalTrials.gov archive [online] NCT02941523 on Oct. 20, 2016, retrieved from https://clinicaltrials.gov/archive/NCT02941523/2016_10 20, on May 2, 2017.

PCT International Search Report and Written Opinion issued in International Application No. PCT/AU2017/050300, dated May 24, 2017.

PCT International Search Report and Written Opinion issued in International Application No. PCT/AU2017/050299, dated May 24, 2017.

PCT International Search Report and Written Opinion issued in International Application No. PCT/AU2017/050363, dated May 25, 2017.

PCT International Search Report and Written Opinion issued in International Application No. PCT/AU2016/050674, dated Aug. 31, 2016.

Postow et al., (2012) "Immunologic Correlates of the Abscopal Effect in a Patient with Melanoma," N. Engl. J. Med., 366:925-31.

Raffoul et al., "Radiosensitization of prostate cancer by soy isoflavones," Current Cancer Drug Targets, 7(8):759-765, 2007.

Reynders et al., (2015) "The abscopal effect of local radiotherapy: using immunotherapy to make a rare event clinically relevant," Cancer Treat. Rev., 41(6): 503-510.

Saif et al., "Flavonoids, phenoxodiol, and a novel agent, triphendiol, for the treatment of pancreaticobiliary cancers," Expert Opinion Investigational Drugs, 18(4):469-79, 2009.

Shin et al., "Sensitization of the apoptotic effect of gamma-irradiation in genistein-pretreated CaSki cervical cancer cells," Journal of Microbiology & Biotechnology, 18(3):523-531, 2008.

Temozolomide prescription information, Feb. 2011 (Year: 2011).

Wang et al., "Prostate Cancer Treatment is Enhanced by Genistein In Vitro and In Vivo in a Syngeneic Orthotopic Tumor Model," Radiation Research, vol. 166, No. 1, Jul. 1, 2006 (Jul. 1, 2006), pp. 73-80, XP55626642, us ISSN: 0033-7587, DOI: 10.1667/RR3590.1.

Yossepowitch et al., "Secondary Therapy, Metastatic Progression, and Cancer-Specific Mortality in Men with Clinically High-Risk Prostate Cancer Treated With Radical Prostatectomy," European Urology, 53(5):950-959, 2008.

Baviskar et al., "Drug delivery on rectal absorption: Suppositories," International Journal of Pharmaceutical Sciences Review and Research, 21(1):70-76, 2013.

Howes et al., "Pharmacokinetic of phenoxodiol, a novel isoflavone, following intravenous administration to patients with advanced cancer," *BMC Clinical Pharmacology*, 11(1):1-8, 2011.

Lipp and Anklam, "Review of cocoa butter and alternative fats for use in chocolate—Part A. Compositional data," *Food Chemistry*, 62(1):73-97, 1998.

National Cancer Institute, "Idronoxil suppository NOX66," *NCI Drug Dictionary* [online], retrieved from https://www.cancer.gov/publications/dictionaries/cancer-drug?cdrid=787307 on May 2, 2017.

Noxopharm Limited, "Phase Ia/Ib and Potential Phase IIa Study of the Safety and Pharmacokinetics of NOX66 Both as a Monotherapy and in Combination With Carboplatin in Patients With Refractory Solid Tumours," ClinicalTrials.gov archive [online] NCT02941523 on Oct. 20, 2016, retrieved from https://clinicaltrials.gov/archive/NCT02941523/2016_10_20, on May 2, 2017.

PCT International Search Report and Written Opinoin issued in International Application No. PCT/AU2017/050301, dated May 25, 2017.

Royal North Shore Hospital, "Phase I Study of Idronoxil Combined With Radiation Treatment in Men With Metastatic Prostate Cancer," ClinicalTrials.gov archive [online], NCT03041285 on Feb. 1, 2017, retrieved from https://clinicaltrials.gov/archive/NCT03041285/2017_02_01 on May 2, 2017.

Ajazuddin et al., "Role of herbal bioactives as a potential bioavailability enhancer for Active Pharmaceutical Ingredients," *Fitoterapia*, 97:1-14, 2014.

Alvero et al., "Anti-tumor activity of phenoxodiol: from bench to clinic," *Future Oncol.*, 4(4):475-482, 2008.

Bandara et al., "Topical isoflavonoids reduce experimental cutaneous inflammation in mice," *Immunology and Cell Biology*, 88(7):727-733, 2010.

Block et al., "Immune System Effects of Echinacea, Ginseng, and Astragalus: A Review," *Integrative Cancer Therapies*, 2(3):247-267, 2003.

Burkard et al., "Dietary flavonoids and modulation of natural killer cells: implications in malignant and viral diseases," *Journal of Nutritional Biochemistry* 46:1-12, 2017.

Diomina, "Classification, nomenclature, and brief description of suppository bases," Development and Registration of Medicinal Products, 2(15):1-10, 2016. (English abstract and English translation of Table 1 of Russian publication).

Fisher et al., "The effect of phospholipid structure on the thermal stability of rhodopsin," *Biochemica et Biophysica Acta*, 707(2):273-279, 1982.

Georgaki, et al., "Phenoxodiol, an anticancer isoflavene, induces immunomodulatory effects in vitro and in vivo," *Journal of Cellular and Molecular Medicine*, 13(9B):3929-3938, 2009.

Mahoney et al., "Cytotoxic effects of the novel isoflavone, phenoxodiol, on prostate cancer cell lines," *J. Biosci.*, 37(1):73-84, 2012.

(56) References Cited

OTHER PUBLICATIONS

Morré et al., "ECTO-NOX Target for the Anticancer Isoflavone Phenoxodiol," *Oncology Research*, 16:299-312, 2007.

Pinato et al., "Evolving concepts in the management of drug resistant ovarian cancer: Dose dense chemotherapy and the reversal of clinical platinum resistance," *Cancer Treat. Rev.*, http://dx.doi.org/10.1016/j.ctrv.2012.04.004. 8 pages. 2012.

Widyarini et al., "Isoflavonoid Compounds from Red Clover (Trifolium pratense) Protect from Inflammation and Immune Suppression Induced by UV Radiation," *Photochemistry and Photobiology*, 74(3):465-470, 2001.

Chakravarty et al., "Flt3L Therapy following Localized Tumor Irradiation Generates Long-Term Protective Immune Response in Metastatic Lung Cancer: Its Implication in Designing a Vaccination Strategy," *Oncology*, 70:245-254, 2006.

Liao et al., "Interleukin-2 at the Crossroads of Effector Responses, Tolerance, and Immunotherapy," *Immunity*, 38(1):13-25, 2013.

Yasuda et al., "Intratumoral injection of interleukin-2 augments the local and abscopal effects of radiotherapy in murine rectal cancer," *Cancer Sci.*, 102(7):1257-1263, 2011.

"Idronoxil (Code C132257)," National Cancer Institute Thesaurus History, available online at https://ncit.nci.nih.gov/ncitbrowser/pages/concept_history.jsf?dictionary=NCI_Thesaurus&version=21.01d&code=C132257, accessed Mar. 4, 2021.

"Idronoxil (Code C2642)," National Cancer Institute Thesaurus History, available online at https://ncit.nci.nih.gov/ncitbrowser/pages/concept_history.jsf?dictionary=NCI_Thesaurus&version=21.01d&code=C2642, accessed Mar. 4, 2021.

Budman et al., "Identification of unique synergistic drug combinations associated with downexpression of surviving in a preclinical breast cancer model system," *Anticancer Drugs*, 23(2):272-279, 2012.

Choueiri et al., "Phase I trial of phenoxodiol delivered by continuous intravenous infusion in patients with solid cancer," *Annals of Oncology*, 17:860-865, 2006.

Kang et al., "Advances in drug delivery system for platinum agents based combination therapy," *Cancer Biol. Med.*, 12:362-374, 2015.

Park et al., "The effect of radiation on the immune response to cancer," *Int. J. Mol. Sci.*, 15:927-943, 2014.

Perez, "Carboplatin in combination therapy for metastatic cancer," *The Oncologist*, 9:518-52, 2004.

Tonekaboni et al., "Predictive approaches for dmg combination discovery in cancer," *Briefings in Bioinformatics*, 19(2):262-276, 2018.

Yaykaci et al., "Phenoxodiol sensitizes metastatic colorectal cancer cells to f-fluorouracil and oxaliplatin-induced apoptosis through intrinsic pathway," *EXCLI Journal*, 19:936-949, 2000.

Nakaya et al., "Potential for immunotherapy combined with cytotoxic chemotherapy/radiotherapy," *Journal of Molecular Targeted Therapy for Cancer*, 13(4):24-28, 2015. (English translation of Japanese publication).

Suzuki et al., "Significance of radiation-induced bystander effects in radiation therapy," *Jpn. J. Med. Phys.*, 34(2):70-78, 2014. (English translation of Japanese publication).

Haywood and Glass, "Compounding for analgesia," *Pharmacist*, 29(1):45-48, 2010.

Marin-Acevedo et al., "Next Generation of immune checkpoint therapy in cancer: new developments and challenges," *Journal of Hematology & Oncology*, 11:39, 20 pages, 2018.

\* cited by examiner

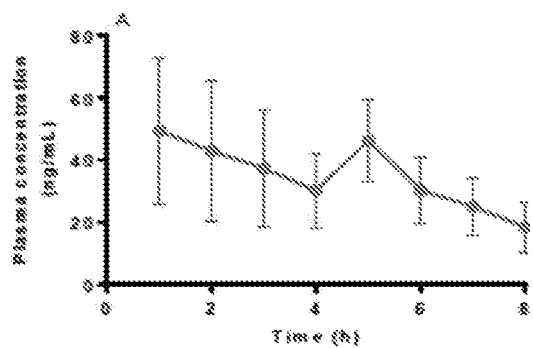 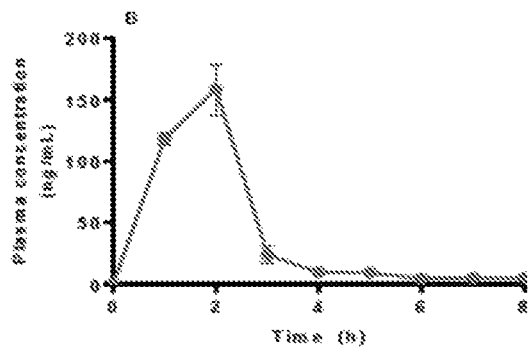

ISOFLAVONOID COMPOSITION WITH IMPROVED PHARMACOKINETICS

This application is a national phase application under 35 U.S.C. § 371 of International Application No. PCT/AU2017/050301, filed Apr. 6, 2017, which claims the priority to U.S. Provisional Patent Application No. 62/318,946, filed Apr. 6, 2016, International Application No. PCT/AU2016/050674, filed Jul. 28, 2016, and to U.S. Provisional Patent Application No. 62/480,692, filed Apr. 3, 2017, the entirety of each are incorporated herein by reference.

FIELD OF THE INVENTION

The invention relates to pharmacokinetics and to dosage schedules applicable to cancer chemotherapy and radiotherapy.

BACKGROUND OF THE INVENTION

Reference to any prior art in the specification is not an acknowledgment or suggestion that this prior art forms part of the common general knowledge in any jurisdiction or that this prior art could reasonably be expected to be understood, regarded as relevant, and/or combined with other pieces of prior art by a skilled person in the art.

Idronoxil [phenoxodiol; dehydroequol, haginin E (2H-1-benzopyran-7-0,1,3-(4-hydroxyphenyl)] is an exemplary compound of a broader class of isoflavonoids that have been considered for the treatment of cancer as a monotherapy, and for sensitising cancer cells to the cytotoxic effects of other compounds and of radiation [Brown D M et al. 2008 *Drugs of the Future* 33(10):844-860]. Other isoflavonoid compounds, such as genistein have also been considered for some of these purposes.

Isoflavonoids including genistein and idronoxil are known to be pleiotropic in their biological functions, the result of blocking phosphorylation of target proteins by a wide range of kinase enzymes. This pleiotropy extends to anti-cancer functions, including both a direct cytotoxic effect and indirect non-lethal effects including sensitising cancer cells to the toxic effects of standard chemotherapy drugs and radiation.

Attempts to develop isoflavonoids as anti-cancer drugs have been unsuccessful regardless of their intended use either as a monotherapy or in combination therapy. To date, no isoflavonoid drug has received marketing approval, reflecting either an inherent lack of efficacy, or a lack of understanding of how best to use this class of drug.

in vitro studies indicate that the likely therapeutic level needed to be achieved in the blood is approximately 1-5 µM (200-1200 ng/mL) [Brown D M et al. 2008 *Drugs of the Future* 33(10):844-860]. This is based both on a reported IC50 value (that is, the concentration of drug required to kill 50% of cancer cells in vitro), as well as a level required to chemo-sensitise standard cytotoxic drugs.

In clinical studies involving humans treated with idronoxil both orally and intravenously, blood levels of 50 µM reportedly are readily attained, including considerably higher levels [Howes J et al. 2011 *BMC Clinical Pharmacol.* 11:1]. That is, purportedly therapeutic blood levels of idronoxil are readily attained and readily exceeded as a function of increasing drug dosage. Despite this, no meaningful anti-cancer effects have yet been reported on any consistent level to support marketing approval.

A likely explanation for this lack of success, despite achieving high peak drug levels in the blood, is the relatively short time that the drug is present at therapeutically effective levels. When given as a bolus IV administration, idronoxil was observed to have a short plasma elimination half-life [Howes J et al. 2011 *BMC Clinical Pharmacol.* 11:1]. This is in contrast to in vitro studies where the drug remains in the culture medium throughout the period of study, but for at least 24 hours A short half-life is not consistent with the known biological effects of idronoxil, particularly as a chemo-sensitising or radio-sensitising agent. While the damage inflicted on the cell by chemotherapy drugs or radiation is an acute and short-lived effect, the response by the tumour cell to that damage is an ongoing process for about 1 week. It is that response that idronoxil targets, suggesting that the presence of idronoxil is required on a constant basis throughout the week or so of response.

This suggests that the idronoxil should be present at therapeutically effective levels for as much of each 24-hour period as possible, preferably for the entire 24 hours. That is, idronoxil ideally would be present in the blood on a steady-state basis.

More particularly, it is believed that if the steady state is not established, there is a significant risk that a chemotherapy or radiotherapy intervention (the effects of which are generally short lived) may not be effectively potentiated, thereby providing a sub-optimal effect. Such an effect might increase the likelihood of resistance to the chemo- or radiotherapy.

As mentioned, various pharmacokinetic assessments for idronoxil describe a compound having a relatively high $C_{max}$, a short $T_{max}$ and a relatively short time to $C_{min}$, suggesting a need to frequently dose (more than twice daily) to obtain the required steady state level. When given as a bolus IV administration, idronoxil was observed to have a short plasma elimination half-life, and the suggestion has been to give idronoxil either as a continuous IV infusion or chronic oral administration [Howes J et al. 2011 *BMC Clinical Pharmacol.* 11:1].

Confusing the issue is that when given orally, idronoxil has a low absolute oral bioavailability. Free idronoxil is detected in plasma within 30 minutes of administration in most patients, but is not consistently above the lower limit of quantitation. Although a conjugated form of idronoxil was observed to have a more preferred PK profile than free idronoxil, the tumour cells are generally resistant to the former [Brown D M et al. 2008 *Drugs of the Future* 33(10):844-860].

Maintenance of a steady-state level of idronoxil by Intravenous injection using a chronic infusion pump is a theoretical possibility, but less certain to be a clinical reality (Choueiri et al, 2006 *Eur. Soc. Med. Oncol.* 17:860-865).

A pharmacokinetic profile that would enable idronoxil and other isoflavonoids to be used effectively to sensitise cells to, and to potentiate the effect of chemo- or radiotherapy is one describing a serum concentration of idronoxil that is within a therapeutic range for at least about 8 hours after administration. Generally the profile would not define a short lived high $C_{max}$, nor a delayed $T_{max}$.

There remains a need for methods and formulations that enable the provision of idronoxil and related isoflavonoids for use in effectively sensitising cells to, and to potentiate the effect of, chemo- or radiotherapy.

There is a need to provide for therapeutic exposure to idronoxil at least 3 hours after administration or longer.

There remains a need to obtain therapeutically effective steady state concentrations of idronoxil and related isoflavonoids, especially in clinical interventions involving chemotherapy or radiotherapy, and wherein the purpose of the steady state concentration of idronoxil or related isoflavonoid is to sensitise cells to the cytotoxic effect of the chemotherapy or radiotherapy.

SUMMARY OF THE INVENTION

In one embodiment there is provided a method for providing in an individual requiring treatment for cancer, a steady state plasma concentration of a compound of Formula I or Formula II of about 20 to 400 ng/mL, the method including the steps of:

a first rectal administration of a suppository formulation, the formulation including: a compound of Formula I or Formula II Formula (I)

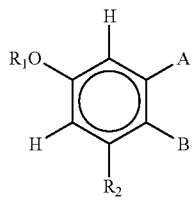
(I)

wherein $R_1$ is H, or $R_ACO$ where $R_A$ is $C_{1-10}$ alkyl or an amino acid;

$R_2$ is H, OH, or $R_B$ where $R_B$ is an amino acid or $COR_A$ where $R_A$ is as previously defined;

A and B together with the atoms between them form a six membered ring selected from the group

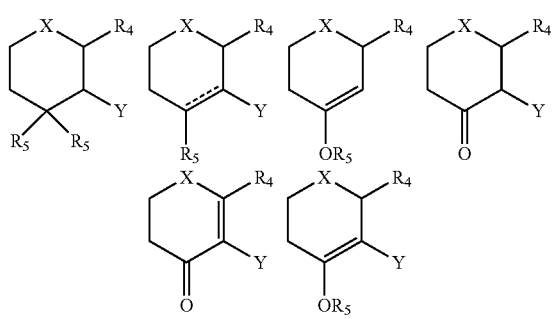

wherein $R_4$ is H, $COR_D$ where $R_D$ is H, OH, $C_{1-10}$ alkyl or an amino acid, $CO_2R_C$ where $R_C$ is $C_{1-10}$ alkyl, $COR_E$ where $R_E$ is H, $C_{1-10}$ alkyl or an amino acid, COOH, $COR_C$ where $R_C$ is as previously defined, or $CONHR_E$ where $R_E$ is as previously defined;

$R_5$ is H, $CO_2R_C$ where $R_C$ is as previously defined, or $COR_COR_E$ where $R_C$ and $R_E$ are as previously defined, and where the two $R_5$ groups are attached to the same group they are the same or different;

X is O, N or S;
Y is

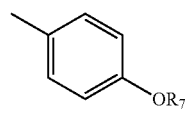

where $R_7$ is H, or $C_{1-10}$ alkyl; and
" $====$ " represents either a single bond or a double bond.

Typically the compound of Formula I is:

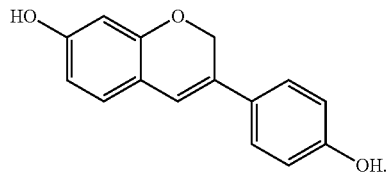

Formula (II)

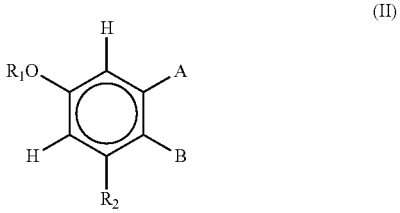
(II)

wherein $R_1$ is H, or $R_ACO$ where $R_A$ is $C_{1-10}$ alkyl or an amino acid;

$R_2$ is H, OH, or $R_B$ where $R_B$ is an amino acid or $COR_A$ where $R_A$ is as previously defined;

A and B together with the atoms between them form the group:

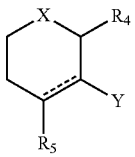

wherein $R_4$ is H, $COR_D$ where $R_D$ is H, OH, $C_{1-10}$ alkyl or an amino acid, $CO_2R_C$ where $R_C$ is $C_{1-10}$ alkyl, $COR_E$ where $R_E$ is H, $C_{1-10}$ alkyl or an amino acid, COOH, $COR_C$ where $R_C$ is as previously defined, or $CONHR_E$ where $R_E$ is as previously defined;

$R_5$ is substituted or unsubstituted aryl or substituted or unsubstituted heteroaryl;

X is O, N or S;
Y is

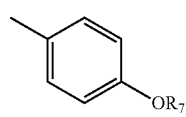

where $R_7$ is H, or $C_{1-10}$ alkyl; and
" $====$ " represents either a single bond or a double bond in an amount of about 6 to 12 mg/kg body weight of the individual, and a lipophilic suppository base;

further rectal administrations of the suppository formulation;

wherein each further rectal administration is no earlier than about 8 hours after a previous rectal administration;

thereby providing in the individual a steady state plasma concentration of a compound of Formula I or Formula II of about 20 to 400 ng/m L.

In another embodiment there is provide a suppository formulation including a compound of Formula I or Formula II described above for use in providing in an individual requiring treatment for cancer, a steady state plasma concentration of a compound of Formula I or Formula II of about 20 to 400 ng/mL, including:

a first rectal administration of a suppository formulation, the formulation including: a compound of Formula I or Formula II in an amount of about 6 to 12 mg/kg body weight of the individual, and a lipophilic suppository base;

further rectal administrations of the suppository formulation;

wherein each further rectal administration is no earlier than about 8 hours after a previous rectal administration;

thereby providing in the individual a steady state plasma concentration of a compound of Formula I or Formula II of about 20 to 400 ng/m L.

In another embodiment there is provided a use of a suppository formulation including a compound of Formula I or Formula II described above for providing in an individual requiring treatment for cancer a steady state plasma concentration of a compound of Formula I or Formula II of about 20 to 400 ng/mL including:

a first rectal administration of a suppository formulation, the formulation including: a compound of Formula I or Formula II in an amount of about 6 to 12 mg/kg body weight of the individual, and a lipophilic suppository base;

further rectal administrations of the suppository formulation;

wherein each further rectal administration is no earlier than about 8 hours after a previous rectal administration;

thereby providing in the individual a steady state plasma concentration of a compound of Formula I or Formula II of about 20 to 400 ng/m L.

In another embodiment there is provided a compound of Formula 1 or Formula II described above for use in the manufacture of a suppository formulation for providing in an individual requiring treatment for cancer, a steady state plasma concentration of a compound of Formula I or Formula II of about 20 to 400 ng/mL, wherein the steady state plasma concentration is established by:

a first rectal administration of a suppository formulation, the formulation including: a compound of Formula I or Formula II in an amount of about 6 to 12 mg/kg body weight of the individual, and a lipophilic suppository base;

further rectal administrations of the suppository formulation;

wherein each further rectal administration is no earlier than about 8 hours after a previous rectal administration.

In another embodiment there is provided a method for providing in an individual requiring treatment for cancer, a steady state plasma concentration of a compound of Formula I or Formula II of about 20 to 400 ng/mL, the method including the steps of:

a first rectal administration of a suppository formulation, the formulation including: a compound of Formula I or Formula II as described herein in an amount of about 1 to 5 mg/kg body weight of the individual, and a lipophilic suppository base;

further rectal administrations of the suppository formulation;

wherein each further rectal administration is no earlier than 4 hours after a previous rectal administration;

thereby providing in the individual a steady state plasma concentration of a compound of Formula I or Formula II of about 20 to 400 ng/mL.

In another embodiment there is provide a suppository formulation including a compound of Formula I or Formula II described above for use in providing in an individual requiring treatment for cancer, a steady state plasma concentration of a compound of Formula I or Formula II of about 20 to 400 ng/mL, including:

a first rectal administration of a suppository formulation, the formulation including: a compound of Formula I or Formula II in an amount of about 1 to 5 mg/kg body weight of the individual, and a lipophilic suppository base;

further rectal administrations of the suppository formulation;

wherein each further rectal administration is no earlier than about 4 hours after a previous rectal administration.

In another embodiment there is provided a use of a suppository formulation including a compound of Formula I or Formula II described above for providing in an individual requiring treatment for cancer a steady state plasma concentration of a compound of Formula I or Formula II of about 20 to 400 ng/mL, including:

a first rectal administration of a suppository formulation, the formulation including: a compound of Formula I or Formula II in an amount of about 1 to 5 mg/kg body weight of the individual, and a lipophilic suppository base;

further rectal administrations of the suppository formulation;

wherein each further rectal administration is no earlier than about 4 hours after a previous rectal administration;

thereby providing in the individual a steady state plasma concentration of a compound of Formula I or Formula II of about 20 to 400 ng/m L.

In another embodiment there is provided a compound of Formula 1 or Formula II described above for use in the manufacture of a suppository formulation for providing in an individual requiring treatment for cancer, a steady state plasma concentration of a compound of Formula I or Formula II of about 20 to 400 ng/mL, wherein the steady state plasma concentration is established by:

a first rectal administration of a suppository formulation, the formulation including: a compound of Formula I or Formula II in an amount of about 1 to 5 mg/kg body weight of the individual, and a lipophilic suppository base;

further rectal administrations of the suppository formulation;

wherein each further rectal administration is no earlier than about 4 hours after a previous rectal administration.

In another embodiment there is provided a method for providing in an individual requiring treatment for cancer, a steady state plasma concentration of a compound of Formula I or Formula II of about 20 to 400 ng/mL, the method including the steps of:

a first rectal administration of a suppository formulation, the formulation including: a compound of Formula I or Formula II as described herein in an amount of about 12 to 25 mg/kg body weight of the individual, and a lipophilic suppository base;

further rectal administrations of the suppository formulation;

wherein each further rectal administration is no earlier than 16 hours after a previous rectal administration;

thereby providing in the individual a steady state plasma concentration of a compound of Formula I or Formula II of about 20 to 400 ng/mL.

In another embodiment there is provide a suppository formulation including a compound of Formula I or Formula II described above for use in providing in an individual requiring treatment for cancer, a steady state plasma concentration of a compound of Formula I or Formula II of about 20 to 400 ng/mL, including:

a first rectal administration of a suppository formulation, the formulation including: a compound of Formula I or Formula II in an amount of about 12 to 25 mg/kg body weight of the individual, and a lipophilic suppository base;

further rectal administrations of the suppository formulation;

wherein each further rectal administration is no earlier than about 16 hours after a previous rectal administration;

thereby providing in the individual a steady state plasma concentration of a compound of Formula I or Formula II of about 20 to 400 ng/mL.

In another embodiment there is provided a use of a suppository formulation including a compound of Formula I or Formula II described above for providing in an individual requiring treatment for cancer a steady state plasma concentration of a compound of Formula I or Formula II of about 20 to 400 ng/mL, including:

a first rectal administration of a suppository formulation, the formulation including: a compound of Formula I or Formula II in an amount of about 12 to 25 mg/kg body weight of the individual, and a lipophilic suppository base;

further rectal administrations of the suppository formulation;

wherein each further rectal administration is no earlier than about 16 hours after a previous rectal administration;

thereby providing in the individual a steady state plasma concentration of a compound of Formula I or Formula II of about 20 to 400 ng/m L.

In another embodiment there is provided a compound of Formula I or Formula II described above for use in the manufacture of a medicament for providing in an individual requiring treatment for cancer, a steady state plasma concentration of a compound of Formula I or Formula II of about 20 to 400 ng/mL, wherein the steady state concentration is established by:

a first rectal administration of a suppository formulation, the formulation including: a compound of Formula I or Formula II in an amount of about 12 to 25 mg/kg body weight of the individual, and a lipophilic suppository base;

further rectal administrations of the suppository formulation;

wherein each further rectal administration is no earlier than about 16 hours after a previous rectal administration.

In another embodiment there is provided a composition including an oleaginous base for use in a device for rectal, vaginal or urethral application a compound of Formula I or II described above.

The oleaginous base may comprise a predominance of (>45% w/w base) saturated fatty acids. Preferably the oleaginous base is Theobroma oil (cocoa butter) or an oil fraction or derivative or synthetic version thereof having a saturated fatty acid profile substantially the same as, or identical to the fatty acid profile of Theobroma oil In another embodiment, the base includes or consists of fatty acids, as described further herein. 50 to 99% of the fatty acids may be saturated fatty acids, about 30 to 50% of fatty acids of the base may be stearic acid, about 20 to 30% of fatty acids of the base may be palmitic acid, about 15-25% of fatty acids of the base may be lauric acid, and about 5 to 10% of fatty acids of the base may be myristic acid.

The composition may contain an amount of compound of Formula I or II of about 1 to 25 mg/kg body weight of an individual, wherein after a single rectal administration of the formulation to a patient there is provided in a plasma sample obtained from the patient at about 3 hours after the single administration of the formulation, a plasma concentration of compound of Formula I or Formula II of about 20 to 400 ng/mL.

In another embodiment there is provided a suppository, pessary, intra-urethral device or like formed from a composition described above In another embodiment there is provided a method for providing in an individual requiring treatment for cancer, a plasma concentration of a compound of Formula I or Formula II as described above that is about 20 to 400 ng/mL at about 3 hours after a single administration of the compound of Formula I or Formula II to the individual, the method including the step of a single rectal administration of a formulation described above to the individual.

In the above described methods and formulations the compound of Formula I may preferably be idronoxil.

BRIEF DESCRIPTION OF THE DRAWINGS

FIG. 1: Plasma concentration-time profiles of idronoxil after rectal (panel A) and intestinal (panel B) administration of idronoxil in cocoa butter and lipid emulsions, respectively, to rats. Data represent mean±SEM for n=3 rats

DETAILED DESCRIPTION OF THE EMBODIMENTS

Reference will now be made in detail to certain embodiments of the invention. While the invention will be described in conjunction with the embodiments, it will be understood that the intention is not to limit the invention to those embodiments. On the contrary, the invention is intended to cover all alternatives, modifications, and equivalents, which may be included within the scope of the present invention as defined by the claims.

One skilled in the art will recognize many methods and materials similar or equivalent to those described herein, which could be used in the practice of the present invention. The present invention is in no way limited to the methods and materials described.

It will be understood that the invention disclosed and defined in this specification extends to all alternative combinations of two or more of the individual features mentioned or evident from the text. All of these different combinations constitute various alternative aspects of the invention.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

A. Rectal Isoflavonoid Pharmacokinetics

The invention particularly relates to formulations and methods that enable the provision of idronoxil and related isoflavonoids for use in effectively sensitising cells to radiotherapy and to chemotherapy, and to potentiating the cytotoxic effect of these therapies on cells, especially cancer cells.

It has been found that rectal delivery of idronoxil provides for a much longer therapeutic exposure of an isoflavonoid in an individual than can be achieved by oral administration. As described herein, in certain embodiments, the amount of idronoxil observed in plasma at 3 to 4 hours after rectal idronoxil administration, is at least 3 to 4 times greater than that observed from oral idronoxil administration.

The methods of the invention described herein enable one to achieve a steady state plasma concentration of idronoxil without the frequent dosing that would otherwise be required by oral administration, and without the impractical intervention that arises from continuous IV infusion. A "steady state" with reference to drug plasma concentration is generally understood as arising where there is equilibrium as between the administration rate and the elimination rate of a drug. Generally at a steady state, drug accumulation is not generally observed, and so there is a lesser risk of exceeding a toxicity threshold. Further, there is a lesser risk of the drug plasma concentration dropping to, or below, $C_{min}$. At a steady state, each dose of a drug should generally provide the same $C_{max}$ and $C_{min}$.

As described herein, the half-life of rectal idronoxil is observed to be longer than 8 hours. This is at least 5 times longer than the half life of oral idronoxil.

The unique pharmacokinetic characteristics of rectal idronoxil are important, particularly for those patients that, because of tumour load, can only be treated with sub-optimal doses of chemotherapy or radiotherapy. In these patients it is critical that there is a radiotherapy or chemotherapy-sensitising plasma concentration of idronoxil or other isoflavonoid at the time that the radiotherapy or chemotherapy is given, otherwise there is a heightened risk that the radiotherapy or chemotherapy will not deliver cytotoxicity to cancer cells, potentially resulting in resistance. The longer exposure to idronoxil that arises from rectal administration increases the likelihood that a radiotherapy or chemotherapy-sensitising plasma concentration of idronoxil will be present in a patient at the time that the individual receives chemo- or radiotherapy.

It is generally well understood that isoflavonoids such as idronoxil are rapidly processed after IV or oral administration, leading to the formation of various metabolites in the form of sulphated or glycosylated isoflavonoid products. These products are generally described as conjugated forms of idronoxil. In these types of administrations very little, if any 'free' or non conjugated idronoxil (i.e. unprocessed idronoxil) can be detected. The distinction is important because conjugated isoflavonoids generally have a reduced activity on tumour cells as compared with non conjugated forms.

In this specification a reference to a plasma concentration of idronoxil or related isoflavonoid refers the concentration of 'free' idronoxil (or related isoflavonoid) i.e. isoflavonoid that has not been subjected to a metabolic process such as phase II metabolism leading to the formation of metabolites of the isoflavonoid. Thus for example, a reference to a plasma concentration of a compound of Formula I or Formula II of about 20 to 400 ng/mL will be understood as meaning a reference to the concentration of the free compound, and not of conjugated compounds. It is possible to discriminate between free and conjugated forms of idronoxil and other isoflavonoids by standard techniques and using the assays described herein.

Thus in one embodiment, there is provided a method for providing in an individual requiring treatment for cancer, a steady state plasma concentration of a compound of Formula I or Formula II of about 20 to 400 ng/mL, the method including the steps of:

a first rectal administration of a suppository formulation, the formulation including: a compound of Formula I or Formula II as described herein in an amount of about 6 to 12 mg/kg body weight of the individual, preferably about 7 or 8 or 9 or 10 mg/kg body weight of the individual, and a lipophilic suppository base;

further rectal administrations of the suppository formulation;

wherein each further rectal administration is no earlier than 8 hours after a previous rectal administration;

thereby providing in the individual a steady state plasma concentration of a compound of Formula I or Formula II of about 20 to 400 ng/mL.

As is generally understood, $C_{min}$ is normally achieved at the completion of about 4 to 5 half lives. Where a threshold toxicity is near $C_{max}$, it is critical to further administer a given drug at the expiry of about the $4^{th}$ or $5^{th}$ half life. Most isoflavonoids have a threshold toxicity that is much higher than $C_{max}$ obtained when dosing between 1 to 20 mg/kg. This means that it is possible to dose isoflavonoids at this amount shortly after a first half life, which according to the invention, is about 8 hours. According to the invention, when given in an amount of about 10 mg/kg, it is possible to dose the compound of Formula I or II at the $2^{nd}$, $3^{rd}$, $4^{th}$ or $5^{th}$ half life, so generally every 16, 24, 32 or 40 hours after a previous administration, respectively. Thus in one embodiment, the compound of Formula I or Formula II as described herein, when given at about 6 to 12 mg/kg is administered no earlier than 8-12 hours after a previous rectal administration. In this embodiment, the compound may be given at 12 hours after a previous rectal administration or shortly, for example, within 1 to 2 hours, preferably within 1 hour, thereafter.

In another embodiment, the compound of Formula I or Formula II as described herein is administered no earlier than 24 hours after a previous rectal administration. In this embodiment, the compound may be given at 24 hours after a previous rectal administration or shortly, for example, within 1 to 2 hours, preferably within 1 hour, thereafter.

In yet another embodiment, the compound of Formula I or Formula II as described herein is administered no earlier than 36 hours after a previous rectal administration. In this embodiment, the compound may be given at 36 hours after a previous rectal administration or shortly, for example, within 1 to 2 hours, preferably within 1 hour, thereafter.

Preferably the amount of compound of Formula I or Formula II provided in each administration according to the above described method is the same.

As will be understood, where the half life or elimination rate of a compound is determined it is possible to determine an administration schedule for a range of doses of the compound. While, according to the invention, an amount of compound of about 6 to 12 mg/kg is preferred, it will be understood that the compound of Formula I or Formula II could be given at other amounts, for example from 1 to 20 mg/kg body weight of recipient or lesser or greater amounts and the time to a further administration to establish a steady state concentration of 20 to 400 ng/mL determined.

Thus in further embodiments, the invention provides a method for providing in an individual requiring treatment for cancer, a steady state plasma concentration of a compound of Formula I or Formula II of about 20 to 400 ng/mL, the method including the steps of:

a first rectal administration of a suppository formulation, the formulation including: a compound of Formula I or Formula II as described herein in an amount of about 1 to 5 mg/kg body weight of the individual, preferably about 2 or 3 or 4 or 5 mg/kg body weight of the individual, and a lipophilic suppository base;

further rectal administrations of the suppository formulation;

wherein each further rectal administration is no earlier than 4 hours after a previous rectal administration;

thereby providing in the individual a steady state plasma concentration of a compound of Formula I or Formula II of about 20 to 400 ng/mL.

In one embodiment, where the formulation includes an amount of about 4 or 5 mg/kg body weight of the individual of a compound of Formula I or Formula II, a further rectal administration may be given no earlier than about 8 hours after a previous rectal administration. In this embodiment, the compound may be given at 8 hours after a previous rectal administration or shortly thereafter, for example, within 1 to 2 hours, preferably within 1 hour, thereafter.

In one embodiment, where the formulation includes an amount of about 4 or 5 mg/kg body weight of the individual of a compound of Formula I or Formula II, a further rectal administration may be given no earlier than about 12 hours after a previous rectal administration. In this embodiment, the compound may be given at 12 hours after a previous rectal administration or shortly, for example, within 1 to 2 hours, preferably within 1 hour, thereafter.

In one embodiment, where the formulation includes an amount of about 4 or 5 mg/kg body weight of the individual of a compound of Formula I or Formula II, a further rectal administration may be given no earlier than about 16 hours after a previous rectal administration. In this embodiment, the compound may be given at 16 hours after a previous rectal administration or shortly, for example, within 1 to 2 hours, preferably within 1 hour, thereafter.

Preferably the amount of compound of Formula I or Formula II provided in each administration according to the above described method is the same.

In a further embodiment, a compound of Formula I or II may be provided in a higher amount of up to 12 to 25 mg/kg body weight or more. Thus there is provided a method for providing in an individual requiring treatment for cancer, a steady state plasma concentration of a compound of Formula I or Formula II of about 20 to 400 ng/mL, the method including the steps of:

a first rectal administration of a suppository formulation, the formulation including: a compound of Formula I or Formula II as described herein in an amount of about 12 to 25 mg/kg body weight of the individual, preferably about 12 or 13 or 14 or 15 mg/kg body weight of the individual, and a lipophilic suppository base;

further rectal administrations of the suppository formulation;

wherein each further rectal administration is no earlier than 12 to 16 hours after a previous rectal administration;

thereby providing in the individual a steady state plasma concentration of a compound of Formula I or Formula II of about 20 to 400 ng/mL.

In one embodiment, where the formulation includes an amount of about 12 or 13 or 14 or 15 mg/kg body weight of the individual of a compound of Formula I or Formula II, a further rectal administration may be given no earlier than about 12 hours after a previous rectal administration. In this embodiment, the compound may be given at 12 hours after a previous rectal administration or shortly, for example within 1 to 2 hours, preferably within 1 hour, thereafter.

In one embodiment, where the formulation includes an amount of about 12 or 13 or 14 or 15 mg/kg body weight of the individual of a compound of Formula I or Formula II, a further rectal administration may be given no earlier than about 24 hours after a previous rectal administration. In this embodiment, the compound may be given at 24 hours after a previous rectal administration or shortly, for example within 1 to 2 hours, preferably within 1 hour, thereafter.

In one embodiment, where the formulation includes an amount of about 12 or 13 or 14 or 15 mg/kg body weight of the individual of a compound of Formula I or Formula II, a further rectal administration may be given no earlier than about 36 hours after a previous rectal administration. In this embodiment, the compound may be given at 36 hours after a previous rectal administration or shortly, for example within 1 to 2 hours, preferably within 1 hour, thereafter.

In one embodiment, where the formulation includes an amount of about 12 or 13 or 14 or 15 mg/kg body weight of the individual of a compound of Formula I or Formula II, a further rectal administration may be given no earlier than about 48 hours after a previous rectal administration. In this embodiment, the compound may be given at 48 hours after a previous rectal administration or shortly, for example, within 1 to 2 hours, preferably within 1 hour, thereafter.

Preferably the amount of compound of Formula I or Formula II provided in each administration according to the above described method is the same.

As described herein, after the first rectal administration of the formulation to a patient there is provided in a plasma sample obtained from the patient at about 4 hours after the first administration of the formulation, a plasma concentration of compound of Formula I or Formula II of about 20 to 400 ng/mL or more. Further in plasma samples obtained from the patient at 4 to 12 hours after the first administration of the formulation, the plasma concentration of compound of Formula I or Formula II may be about 20 to 400 ng/m L.

In the above described embodiments, the amount of compound of Formula I or Formula II provided in each administration may be from 100 to 1600 mg, for example 100 mg, 200 mg, 300 mg, 400 mg, 500 mg, 600 mg, 700 mg, 800 mg, 900 mg, 1000 mg, 1100 mg, 1200 mg, 1300 mg, 1400 mg, 1500 mg, or 1600 mg.

A single administration may involve the administration of a single suppository or more than one suppository. Typically an administration consists of the administration of a single suppository.

A suppository may contain 400 mg or 800 mg of compound of Formula I or Formula II, or from 100 to 350 mg, or from 450 to 750 mg or from 850 to 1550 mg.

Typically the lipophilic suppository base includes or consists of fatty acids, as described further herein. In one embodiment, 50 to 99% of the fatty acids are saturated fatty acids. In another embodiment, about 30 to 50% of fatty acids of the base are stearic acid, about 20 to 30% of fatty acids of the base are palmitic acid, about 15-25% of fatty acids of the base are lauric acid, about 5 to 10% of fatty acids of the base are myristic acid.

In a particular embodiment, the compound of Formula 1 is idronoxil.

In one embodiment, the compound of Formula I or Formula II may be partially or wholly dissolved in the suppository base.

As described further herein, the individual the subject of the method may be one who is to receive chemotherapy or radiotherapy for treatment of cancer and the steady state plasma concentration of the isoflavonoid potentiates a cytotoxic effect of the chemotherapy or radiotherapy. In this embodiment, the steady state plasma concentration of the isoflavonoid is provided for the duration of the chemotherapy or radiotherapy treatment.

In a particular embodiment, the method includes the further step of assessing a plasma sample obtained from the patient at about 3 to 12 hours after the first or subsequent rectal administrations to determine whether the plasma concentration of free isoflavonoid in the sample is from about 20 to 400 ng/mL. This step enables the clinician to ensure that at the time that a chemotherapy or radiotherapy is to be given there is a sufficient plasma concentration of idronoxil or related isoflavonoid for potentiating the effect of the chemo or radiotherapy. Such an assessment of the plasma sample may then be utilised to determine the timing of radio or chemotherapy. In one embodiment, a sample is assessed at about 3 hours after the first rectal administration of the formulation. In another embodiment, a sample is assessed at about 3 hours after every subsequent rectal administration of the formulation. In yet a further embodiment, a sample is assessed at about 3 hours after every $2^{nd}$ or $3^{rd}$ administration of the formulation.

In one embodiment there is provided a method for providing in an individual requiring treatment for cancer, a steady state plasma concentration of idronoxil of about 20 to 400 ng/mL, the method including the steps of:

a first rectal administration of a suppository formulation, the formulation including: idronoxil in an amount of about 6 to 12 mg/kg body weight of the individual, and a lipophilic suppository base;

further rectal administrations of the suppository formulation;

wherein each further rectal administration is no earlier than 8 hours after a previous rectal administration;

thereby providing in the individual a steady state plasma concentration of idronoxil of about 20 to 400 ng/mL.

In another embodiment, there is provided a method for providing in an individual requiring treatment for cancer, a plasma concentration of a compound of Formula I or Formula II, preferably idronoxil, that is about 20 to 400 ng/mL at about 3 hours after a single administration of the compound of Formula I or Formula II to the individual, the method including the step of a single rectal administration of a formulation described herein to the individual. The method may include the further step of assessing a plasma sample obtained from the patient at about 3 hours after the single administration of the formulation to determine the plasma concentration of compound of Formula I or Formula II in the sample.

B. Compounds of Formula I and II

The compounds of Formula I and Formula II may be referred to as isoflavonoids as generally described below:

Formula I

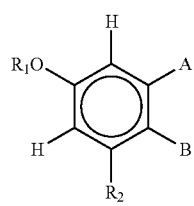
(I)

wherein $R_1$ is H, or $R_A CO$ where $R_A$ is $C_{1-10}$ alkyl or an amino acid;

$R_2$ is H, OH, or $R_B$ where $R_B$ is an amino acid or $COR_A$ where $R_A$ is as previously defined;

A and B together with the atoms between them form a six membered ring selected from the group

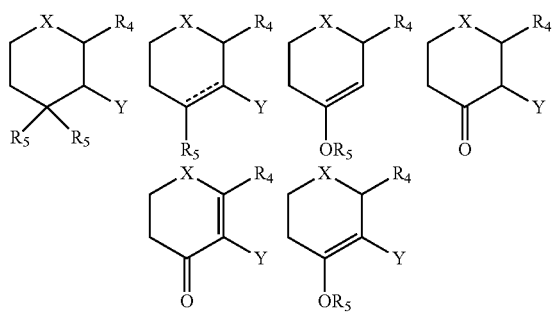

wherein $R_4$ is H, $COR_D$ where $R_D$ is H, OH, $C_{1-10}$ alkyl or an amino acid, $CO_2R_C$ where $R_C$ is $C_{1-10}$ alkyl, $COR_E$ where $R_E$ is H, $C_{1-10}$ alkyl or an amino acid, COOH, $COR_C$ where $R_C$ is as previously defined, or $CONHR_E$ where $R_E$ is as previously defined;

$R_5$ is H, $CO_2R_C$ where $R_C$ is as previously defined, or $COR_COR_E$ where $R_C$ and $R_E$ are as previously defined, and where the two $R_5$ groups are attached to the same group they are the same or different;

X is O, N or S;

Y is

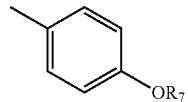

where $R_7$ is H, or $C_{1-10}$ alkyl; and

" ==== " represents either a single bond or a double bond.

Preferably, X is O.

In preferred embodiments, the compound of formula (I) is selected from the group consisting of

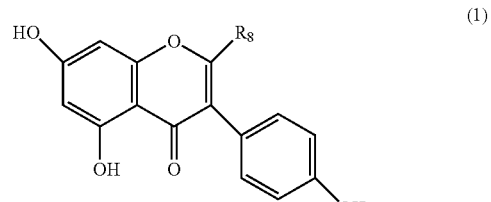
(1)

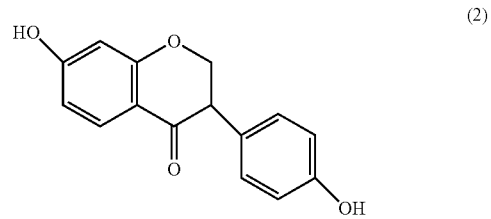
(2)

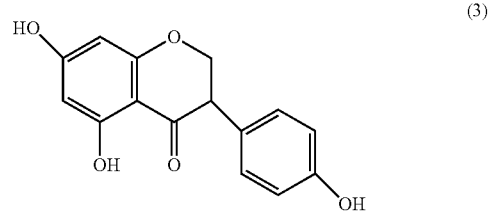
(3)

-continued (4) 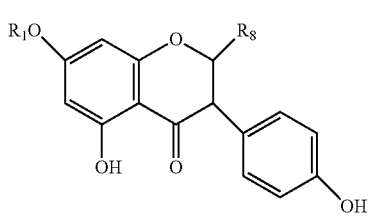

(5) 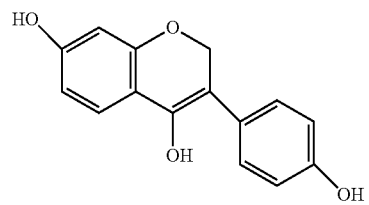

(6) 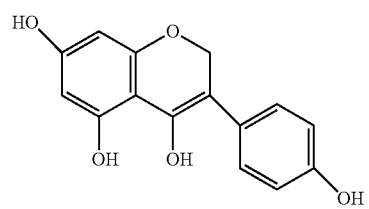

(7) 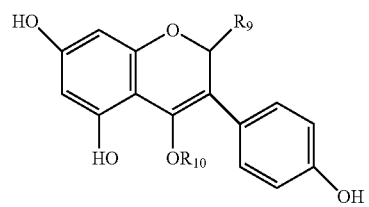

(8) 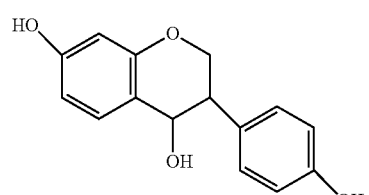

(9) 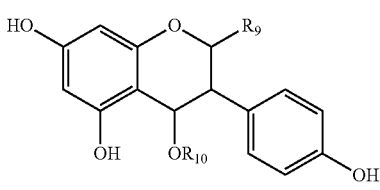

(10) 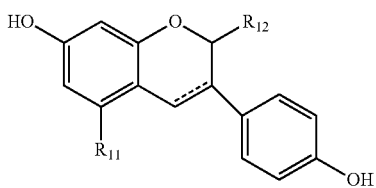

wherein
$R_8$ is H or $COR_D$ where $R_D$ is as previously defined;
$R_9$ $CO_2R_C$ or $COR_E$ where $R_C$ and $R_E$ are as previously defined;
$R_{10}$ is $COR_C$ or $COR_COR_E$ where $R_C$ and $R_E$ are as previously defined;
$R_{11}$ is H or OH;
$R_{12}$ is H, COOH, $CO_2R_C$ where $R_C$ and is as previously defined, or $CONHR_E$ where $R_E$ is as previously defined; and "=====" represents either a single bond or a double bond.
Preferably, the compound of Formula (I) is

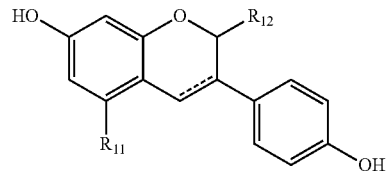

wherein $R_{11}$ and $R_{12}$ are as defined above.
Even more preferably, the compound of Formula (I) is

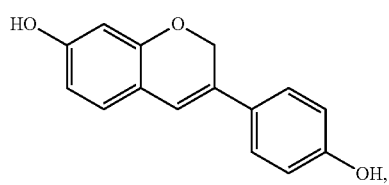 [SMILES: Oc1ccc(C2=Cc3ccc(O)cc3OC2)cc1]

otherwise known as idronoxil (also known as phenoxodiol; dehydroequol; Haginin E (2H-1-Benzopyran-7-0, 1,3-(4-hydroxyphenyl)).

In another aspect, the isoflavonoids for use in a composition according to the invention described are shown by Formula (II):

(II)

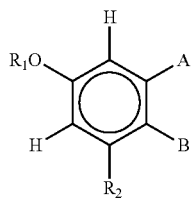

wherein
$R_1$ is H, or $R_ACO$ where $R_A$ is $C_{1-10}$ alkyl or an amino acid;
$R_2$ is H, OH, or $R_B$ where $R_B$ is an amino acid or $COR_A$ where $R_A$ is as previously defined;
A and B together with the atoms between them form the group:

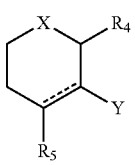

wherein
$R_4$ is H, $COR_D$ where $R_D$ is H, OH, $C_{1-10}$ alkyl or an amino acid, $CO_2R_C$ where $R_C$ is $C_{1-10}$ alkyl, $COR_E$ where $R_E$ is H, $C_{1-10}$ alkyl or an amino acid, COOH, $COR_C$ where $R_C$ is as previously defined, or $CONHR_E$ where $R_E$ is as previously defined;
$R_5$ is substituted or unsubstituted aryl or substituted or unsubstituted heteroaryl;
X is O, N or S;

Y is

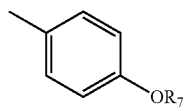

where R$_7$ is H, or C$_{1-10}$ alkyl; and
"=====" represents either a single bond or a double bond.

In one preferred embodiment, R$_5$ is aryl substituted with an alkoxy group. Preferably, the alkoxy group is methoxy. In another preferred embodiment, R$_5$ is hydroxy.

In preferred embodiments, the compound of formula (II) is

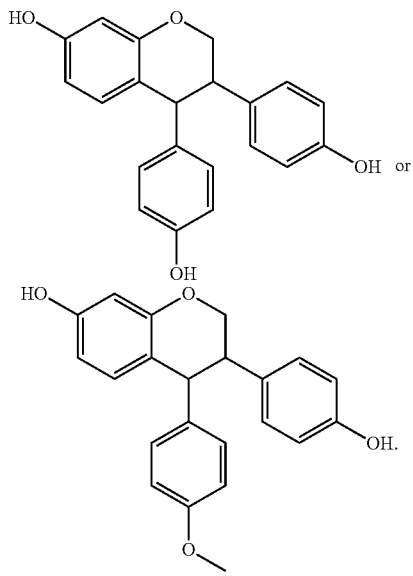

As used herein the term "alkyl" refers to a straight or branched chain hydrocarbon radical having from one to ten carbon atoms, or any range between, i.e. it contains 1, 2, 3, 4, 5, 6, 7, 8, 9 or 10 carbon atoms. The alkyl group is optionally substituted with substituents, multiple degrees of substitution being allowed. Examples of "alkyl" as used herein include, but are not limited to, methyl, ethyl, n-propyl, isopropyl, n-butyl, isobutyl, t-butyl, n-pentyl, isopentyl, and the like.

As used herein, the term "C$_{1-10}$ alkyl" refers to an alkyl group, as defined above, containing at least 1, and at most 10 carbon atoms respectively, or any range in between (e.g. alkyl groups containing 2-5 carbon atoms are also within the range of C$_{1-10}$).

Preferably the alkyl groups contain from 1 to 5 carbons and more preferably are methyl, ethyl or propyl.

As used herein, the term "aryl" refers to an optionally substituted benzene ring. The aryl group is optionally substituted with substituents, multiple degrees of substitution being allowed.

As used herein, the term "heteroaryl" refers to a monocyclic five, six or seven membered aromatic ring containing one or more nitrogen, sulfur, and/or oxygen heteroatoms, where N-oxides and sulfur oxides and dioxides are permissible heteroatom substitutions and may be optionally substituted with up to three members. Examples of "heteroaryl" groups used herein include furanyl, thiophenyl, pyrrolyl, imidazolyl, pyrazolyl, triazolyl, tetrazolyl, thiazolyl, oxazolyl, isoxazolyl, oxadiazolyl, oxo-pyridyl, thiadiazolyl, isothiazolyl, pyridyl, pyridazyl, pyrazinyl, pyrimidyl and substituted versions thereof.

A "substituent" as used herein, refers to a molecular moiety that is covalently bonded to an atom within a molecule of interest. For example, a "ring substituent" may be a moiety such as a halogen, alkyl group, or other substituent described herein that is covalently bonded to an atom, preferably a carbon or nitrogen atom, that is a ring member. The term "substituted," as used herein, means that any one or more hydrogens on the designated atom is replaced with a selection from the indicated substituents, provided that the designated atom's normal valence is not exceeded, and that the substitution results in a stable compound, i.e., a compound that can be isolated, characterised and tested for biological activity.

The terms "optionally substituted" or "may be substituted" and the like, as used throughout the specification, denotes that the group may or may not be further substituted, with one or more non-hydrogen substituent groups. Suitable chemically viable substituents for a particular functional group will be apparent to those skilled in the art.

Examples of substituents include but are not limited to:

C$_1$-C$_6$ alkyl, C$_1$-C$_6$ haloalkyl, C$_1$-C$_6$ haloalkoxy, C$_1$-C$_6$ hydroxyalkyl, C$_3$-C$_7$ heterocyclyl, C$_3$-C$_7$ cycloalkyl, C$_1$-C$_6$ alkoxy, C$_1$-C$_6$ alkylsulfanyl, C$_1$-C$_6$ alkylsulfenyl, C$_1$-C$_6$ alkylsulfonyl, C$_1$-C$_6$ alkylsulfonylamino, arylsulfonoamino, alkylcarboxy, alkylcarboxyamide, oxo, hydroxy, mercapto, amino, acyl, carboxy, carbamoyl, aminosulfonyl, acyloxy, alkoxycarbonyl, nitro, cyano or halogen.

The term "isoflavonoid" as used herein is to be taken broadly and includes isoflavones, isoflavenes, isoflavans, isoflavanones, isoflavanols and similar or related compounds. Some non-limiting examples of isoflavonoid core structures are shown below:

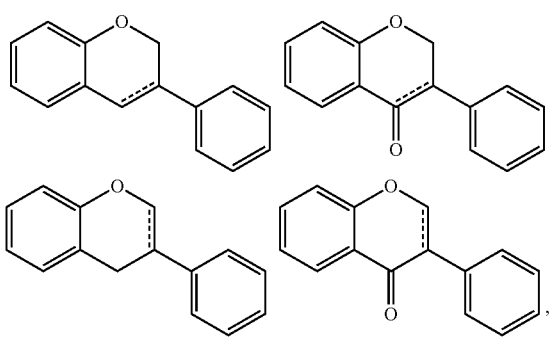

wherein "=====" represents either a single bond or a double bond.

Some of the compounds discussed above may be referred to by the names dihydrodaidzein (compound 1 where R$_8$ is H), dihydrogenestein (compounds 2 and 5), tetrahydrodaidzein (compound 8) and equol and dehydroequol (compound 10).

Methods for synthesis of the above described compounds are described in WO1998/008503 and WO2005/049008 and references cited therein towards the synthesis, the contents of which are incorporated herein by reference in entirety.

C. Bases for Forming Suppository, Pessary or Urethral Devices

Without being bound by hypothesis, it is believed that oleaginous bases (i.e. hydrophobic or lipophilic bases) enable the therapeutic effect of an isoflavonoid, whereas hydrophilic bases, such as PEG, cyclodextrin and the like do not.

In the disclosure below, 'base' may refer to a substance commonly used as a carrier in a suppository, pessary or intra-urethral device.

Generally the base has a solvent power for the isoflavonoid enabling at least partial, preferably complete dissolution of the isoflavonoid in the base.

The base may be comprised of, or consist of an oil or fat.

In one embodiment the base includes saturated fatty acids in an amount of 50 to 65% w/w base. Stearic acid may be included in an amount of 25 to 40% w/w base. Palmitic acid may be included in an amount of 25 to 30% w/w base. Longer chain saturated fatty acids such as myristic, arachidic and lauric acid may be included in an amount of <2% w/w base.

Further described herein, it has been found that oleaginous bases that are high in unsaturated fatty acids tend to be less advantageous in the invention. Typically, the oleaginous base includes unsaturated fatty acids in an amount of 35 to 50% w/w base. Monounsaturated fatty acid may be included in an amount of 30 to 45% w/w base. Oleic acid may be included in an amount of 30 to 40% w/w base. Polyunsaturated fatty acids such as linoleic and alpha linolenic acid may be included in an amount of 0 to 5% w/w base.

Theobroma oil (cocoa butter) has been a traditional base in a suppository because of: (a) its non-toxic and non-irritant nature, and (b) its low melting point, meaning that it readily dissolves at body temperature when placed within a bodily cavity, However, it is increasingly being replaced for a number of reasons. One reason is its variability in composition, a consequence of its natural origins; theobroma oil also is polymorphic, meaning it has the ability to exist in more than one crystal form. Another is that the formulated product needs to be kept refrigerated because of its low melting point, rendering it unsuitable in tropical regions. This has led to a number of substitute products offering a range of advantages over theobroma oil such as greater consistency, decreased potential for rancidity, and greater ability to tailor phase transitions (melting and solidification) to specific formulation, processing, and storage requirements.

Nevertheless, theobroma oil or a fatty base with similar composition and physico-chemical properties has been found to be a preferred embodiment of the invention.

Typically the oleaginous base comprises a predominance of (>45% w/w base) of saturated fatty acids. Preferably the oleaginous base is Theobroma oil (cocoa butter) or an oil fraction or derivative or synthetic version thereof having a saturated fatty acid profile substantially the same as, or identical to the fatty acid profile of Theobroma oil.

Other examples of oils that may be used to provide or obtain fatty acids useful as bases include those obtainable from natural sources such as canola oil, palm oil, soya bean oil, vegetable oil, and castor oil. Oils derived from these sources may be fractionated to obtain oil fractions containing saturated fatty acids.

The base may be formed or derived from a hard fat, butter or tallow.

A base may comprise esterified or non-esterified fatty acid chains. The fatty acid chains may be in the form of mono, di and trigycerides, preferably of saturated fatty acid chains of C9-20 chain length.

A suppository base may be formed from synthetic oils or fats, examples including Fattibase, Wecobee, Witepesoll (Dynamit Nobel, Germany), Suppocire (Gatefosse, France, Hydrokote and Dehydag.

The proportion of the oleaginous suppository base in the final product is a function of the dosage of active pharmaceutical ingredient and the presence of other pharmaceutical or inert ingredient (if any) but may be provided by way of example in an amount of about 1 to 99% w/w formulation.

In one embodiment the lipophilic suppository base contains fatty acids and wherein 50 to 100% of the fatty acids of the base are saturated fatty acids, preferably, 90 to 99% of the fatty acids of the base are saturated fatty acids. 30 to 60%, preferably about 40% of fatty acids of the base may be stearic acid. 20 to 30%, preferably about 25% of fatty acids of the base may be palmitic acid. 15 to 25%, preferably about 20% of fatty acids of the base may be lauric acid. 5 to 10%, preferably about 8% of fatty acids of the base may be myristic acid.

D. Manufacture

The isoflavonoid suppository, pessary and devices for urethral application of the invention may be prepared as follows. The isoflavonoid is contacted with a suppository base (as described above) in molten form in conditions enabling at least partial, preferably complete or substantially complete dissolution of the isoflavonoid in the base.

This solution is then poured into a suitable mould, such as a PVC, polyethylene, or aluminium mould. For example, the isoflavonoid may be contacted with the base at a temperature of from about 35° C. to about 50° C. and preferably from about 40° C. to about 44° C. The isoflavonoid can be milled or sieved prior to contact with the base.

In one embodiment, the conditions provided for manufacture, and formulation or device formed from same, enable at least, or provide at least, 50%, preferably 60%, preferably 70%, preferably 80%, preferably 90%, preferably 95% of the isoflavonoid for a given dosage unit to be dissolved in the dosage unit. In these embodiments, no more than 50% of the isoflavonoid for a given dosage unit, preferably no more than 40%, preferably no more than 30%, preferably no more than 20%, preferably no more than 10%, preferably no more than 5% of isoflavonoid for a given dosage unit may be in admixture with, (i.e. undissolved in) the suppository base of the dosage unit.

In a preferred embodiment, all of the isoflavonoid added to a dosage unit is dissolved in the base. In this embodiment, no isoflavonoid is left in admixture with the suppository base. This is believed to increase the likelihood of the uptake of all of the isoflavonoid given in the dosage unit.

It will be understood that the objective of the manufacture process is not to admix, or to mingle, or to blend the suppository base with the isoflavonoid as generally occurs in pharmacy practice of admixing components, as it is believed that the resulting admixture would have a lower likelihood of providing therapeutic benefit. In this context, it is particularly important that any other excipient, carrier or other pharmaceutical active does not interfere with the dissolution of the isoflavonoid in the base, for example as may occur if the isoflavonoid forms a complex with a charged molecular species (other pharmaceutical active, carrier or excipient), the result of which would be to decrease the propensity of the complex, and therefore the isoflavonoid contained in it, to dissolve in the suppository base.

Optionally the suppositories, pessaries or intra-urethral devices may be coated, prior to packing, for example with cetyl alcohol, macrogol or polyvinyl alcohol and polysorbates to increase disintegration time or lubrication or to reduce adhesion on storage.

One or more sample suppositories, pessaries, or intra-urethral devices from each batch produced are preferably tested by the dissolution method of the present invention for quality control. According to a preferred embodiment, a sample from each batch is tested to determine whether at least about 75 or 80% by weight of the base dissolves within 2 hours.

Typically the suppository, pessary or like device according to the invention is substantially hydrophobic or lipophilic throughout and does not contain a hydrophilic substance such as hydrophilic carrier or pharmaceutical active, or hydrophilic foci or region formed from the ligation or complexing of the isoflavonoid to or with another pharmaceutical compound, carrier or excipient.

Preferably the formulation for forming the suppository, pessary and devices for urethral application does not include a further pharmaceutical active, cytotoxic or chemotherapeutic agent. In this embodiment, the only active is the isoflavonoid and the formulation does not include a platin, taxane or other cytotoxic or chemotherapeutic agent.

E. Formulations

In one embodiment, there is provided a suppository, pessary or urethral device formulation including
 a compound of Formula I or Formula II;
 a suppository base; and
 wherein after a single rectal administration of the formulation to a patient there is provided in a plasma sample obtained from the patient at about 3 hours after the single administration of the formulation, a plasma concentration of compound of Formula I or Formula II of about 20 to 400 ng/mL.

Preferably the compound is idronoxil.

In one embodiment, the formulation provides in plasma samples obtained from the patient at 4 to 12 hours after the single rectal administration of the formulation, a plasma concentration of compound of Formula I or Formula II of about 20 to 400 ng/mL.

In one embodiment, the compound of Formula I or Formula II is provided in a suppository, pessary or urethral device formed from the formulation in an amount of from about 400 to 800 mg.

In another embodiment, the compound of Formula I or Formula II is provided in a suppository or pessary or urethral device formed from the formulation in an amount 100 to 350 mg, or about 450 to 750 mg, or about 900 to 1500 mg.

The total weight of the suppository preferably ranges from about 2250 to about 2700 mg and more preferably from about 2250 to about 2500 mg. According to one embodiment, the suppository has a total weight ranging from about 2300 mg to about 2500 mg.

The suppository or pessary is preferably smooth torpedo-shaped.

The melting point of the suppository or pessary is generally sufficient to melt in the patient's body, and is typically no more than about 37° C.

In one particularly preferred embodiment there is provided:
 a kit including:
  a plurality of suppositories sufficient in number to provide an individual with a suppository once daily, or twice daily, for a period of 30 to 90 days, preferably 30 to 60 days, preferably 30 days
  each suppository including:
   400 mg or 800 mg of idronoxil;
   a suppository base in the form of cocoa butter;
   wherein the suppository base in provided an amount of 1-99% w/w of the suppository,
 the kit further including:
  written instructions to provide the suppository once daily, or twice daily for a period of 30 to 90 days, preferably 30 to 60 days, preferably 30 days, preferably for use in treatment of cancer, more preferably for sensitising cancer cells to cytotoxic effect of a chemo- or radiotherapy, preferably where the cancer is prostate cancer.

In another embodiment there is provided a composition including:
 an oleaginous base for use in a device for rectal, vaginal or urethral application;
 a compound of Formula I contained or dissolved in the base

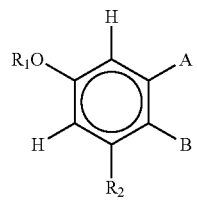

(I)

wherein $R_1$ is H, or $R_A CO$ where $R_A$ is $C_{1-10}$ alkyl or an amino acid;

$R_2$ is H, OH, or $R_B$ where $R_B$ is an amino acid or $COR_A$ where $R_A$ is as previously defined;

A and B together with the atoms between them form a six membered ring selected from the group consisting of:

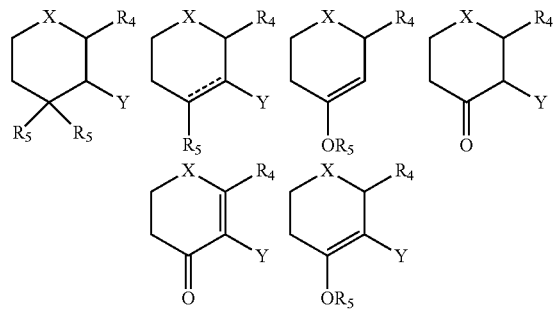

wherein $R_4$ is H, $COR_D$ where $R_D$ is H, OH, $C_{1-10}$ alkyl or an amino acid, $CO_2R_C$ where $R_C$ is $C_{1-10}$ alkyl, $COR_E$ where $R_E$ is H, $C_{1-10}$ alkyl or an amino acid, COOH, $COR_C$ where $R_C$ is as previously defined, or $CONHR_E$ where $R_E$ is as previously defined;

$R_5$ is H, $CO_2R_C$ where $R_C$ is as previously defined, or $COR_COR_E$ where $R_C$ and $R_E$ are as previously defined, and where the two $R_5$ groups are attached to the same group they are the same or different;

X is O, N or S;

Y is

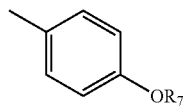

where $R_7$ is H, or $C_{1-10}$ alkyl; and
"=====" represents either a single bond or a double bond.

In one embodiment, X is O.

In another embodiment, the compound of formula (I) of the composition is selected from the group consisting of

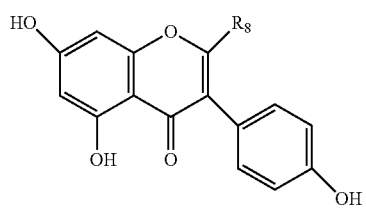
(1)

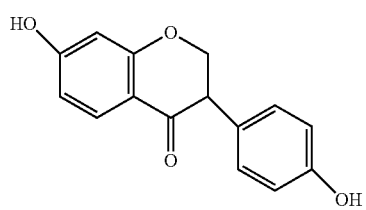
(2)

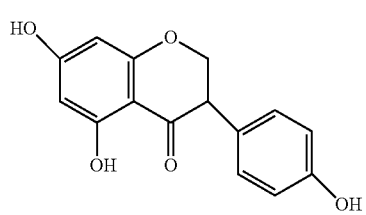
(3)

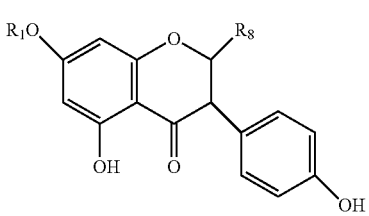
(4)

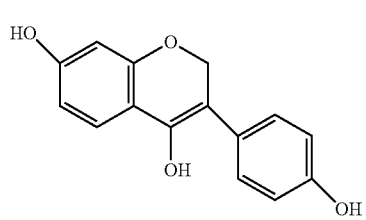
(5)

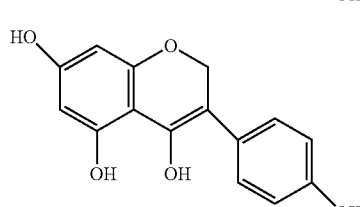
(6)

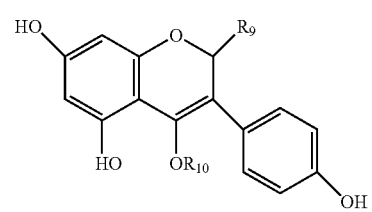
(7)

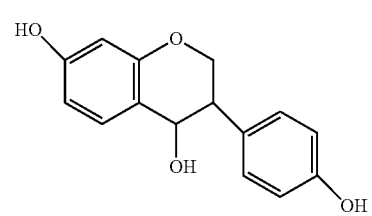
(8)

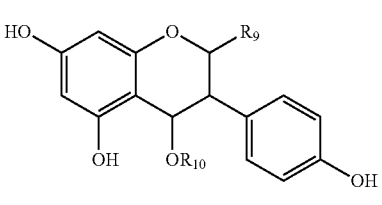
(9)

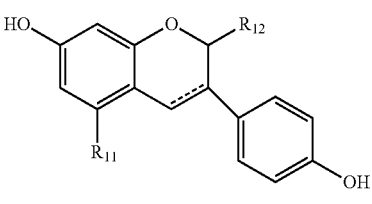
(10)

wherein $R_8$ is H or $COR_D$ where $R_D$ is as previously defined;

$R_9$ $CO_2R_C$ or $COR_E$ where $R_C$ and $R_E$ are as previously defined;

$R_{10}$ is $COR_C$ or $COR_COR_E$ where $R_C$ and $R_E$ are as previously defined;

$R_{11}$ is H or OH;

$R_{12}$ is H, COOH, $CO_2R_C$ where $R_C$ and is as previously defined, or $CONHR_E$ where $R_E$ is as previously defined; and "=====" represents either a single bond or a double bond.

In another embodiment, the compound of formula (I) of the composition is

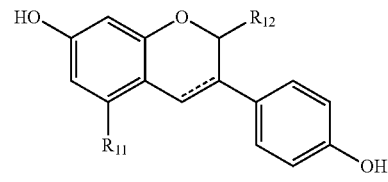

wherein $R_{11}$ and $R_{12}$ are as defined above.

In another embodiment, the compound of formula (I) of the composition is

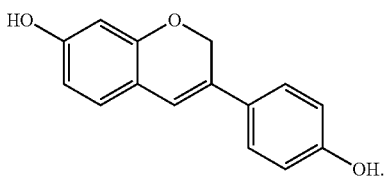 [SMILES: Oc1ccc(C2=Cc3ccc(O)cc3OC2)cc1]

In another embodiment there is provided a composition including:
an oleaginous base for use in a device for rectal, vaginal or urethral application;
a compound of Formula II contained or dissolved in the base (II)

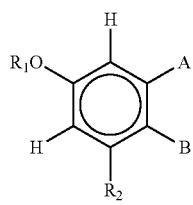

wherein $R_1$ is H, or $R_A CO$ where $R_A$ is $C_{1-10}$ alkyl or an amino acid;

$R_2$ is H, OH, or $R_B$ where $R_B$ is an amino acid or $COR_A$ where $R_A$ is as previously defined;

A and B together with the atoms between them form the group:

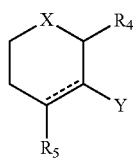

wherein $R_4$ is H, $COR_D$ where $R_D$ is H, OH, $C_{1-10}$ alkyl or an amino acid, $CO_2 R_C$ where $R_C$ is $C_{1-10}$ alkyl, $COR_E$ where $R_E$ is H, $C_{1-10}$ alkyl or an amino acid, COOH, $COR_C$ where $R_C$ is as previously defined, or $CONHR_E$ where $R_E$ is as previously defined;

$R_5$ is substituted or unsubstituted aryl or substituted or unsubstituted heteroaryl;

X is O, N or S;

Y is

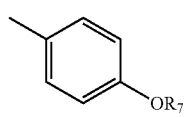

where $R_7$ is H, or $C_{1-10}$ alkyl; and
" ==== " represents either a single bond or a double bond.

In one embodiment, X is O.

In another embodiment, the compound of formula (II) of the composition is

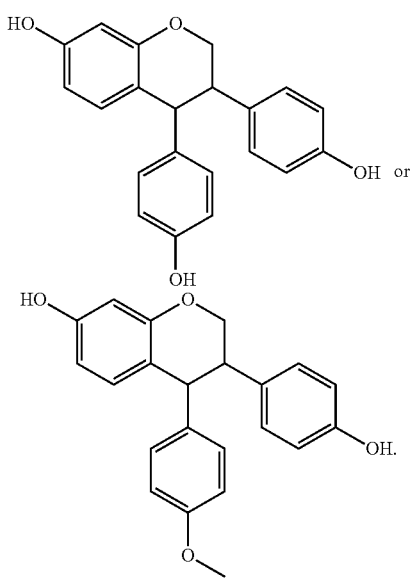

The compounds of Formula I or II may be provided in the formulation in an amount of from 0.1 to 20 w/w % formulation, preferably an amount of 15 w/w % formulation.

The oleaginous base may be provided in the formulation in an amount of about 1 to 99% w/w formulation.

The oleaginous base includes saturated fatty acids in an amount of 50 to 65% w/w base, for example up to 98% or 99% w/w base.

The oleaginous base may include stearic acid in an amount of 25 to 40% w/w base. The oleaginous base may include palmitic acid in an amount of 25 to 30% w/w base. The oleaginous base may include includes myristic, arachidic and lauric acid in an amount of <2% w/w base, although higher amounts of these compounds are possible, in particular about 20% of fatty acids of the base may be lauric acid, and/or 5 to 10%, of fatty acids of the base may be myristic acid.

The oleaginous base may include unsaturated fatty acids in an amount of 35 to 50% w/w base.

The oleaginous base may include monounsaturated fatty acid in an amount of 30 to 45% w/w base.

The oleaginous base may include oleic acid in an amount of 30 to 40% w/w base.

The oleaginous base may include polyunsaturated fatty acids in an amount of 0 to 5% w/w base.

In another embodiment there is provided a suppository, pessary or like formed from a composition described above. Preferably the suppository includes the compound

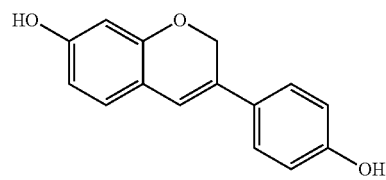 [SMILES: Oc1ccc(C2=Cc3ccc(O)cc3OC2)cc1]

in an amount of about 40-800 mg. The suppository may have an oleaginous base including Theobroma oil in an amount of about 1-99 w/w % of the suppository. The compound of Formula I may be dissolved in the oleaginous base.

F. Methods of Treatment

The formulations according to the invention in suppository, pessary, intra-urethral device or like form are useful for improving the bioavailability of isoflavonoids in a range of therapeutic applications.

In one particularly preferred embodiment, the formulations are useful for treatment of cancer, whereby the isoflavonoid is used as a cytotoxic monotherapy, or as a chemosensitising agent for another cytotoxic molecule.

Thus in one embodiment there is provided a method of treating or preventing cancer in an individual, including administering to a person in need thereof a suppository, pessary or intra-urethral device formed from a formulation according to the invention.

In one embodiment there is provided a use of a formulation according to the invention in the preparation of a suppository, pessary or intra-urethral device for the prevention or treatment of cancer.

In another embodiment there is provided a suppository, pessary or intra-urethral device formed from a formulation according to the invention for use in preventing or treating cancer.

Methods for applying a suppository are well known in the art. Generally the methods involve inserting the suppository to a point aligned with the inferior and medial haemorrhoid veins, thereby enabling the release of the drug to the inferior vena cave.

Methods for applying a pessary, or for urethral application of a pharmaceutically active ingredient are well known in the art.

'Treatment' generally refers to both therapeutic treatment and prophylactic or preventative measures.

Subjects requiring treatment include those already having a benign, pre-cancerous, or non-metastatic tumor as well as those in which the occurrence or recurrence of cancer is to be prevented.

The objective or outcome of treatment may be to reduce the number of cancer cells; reduce the primary tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the disorder.

Efficacy of treatment can be measured by assessing the duration of survival, time to disease progression, the response rates (RR), duration of response, and/or quality of life.

In one embodiment, the method is particularly useful for delaying disease progression.

In one embodiment, the method is particularly useful for extending survival of the human, including overall survival as well as progression free survival.

In one embodiment, the method is particularly useful for providing a complete response to therapy whereby all signs of cancer in response to treatment have disappeared. This does not always mean the cancer has been cured.

In one embodiment, the method is particularly useful for providing a partial response to therapy whereby there has been a decrease in the size of one or more tumors or lesions, or in the extent of cancer in the body, in response to treatment.

"Pre-cancerous" or "pre-neoplasia" generally refers to a condition or a growth that typically precedes or develops into a cancer. A "pre-cancerous" growth may have cells that are characterized by abnormal cell cycle regulation, proliferation, or differentiation, which can be determined by markers of cell cycle.

In one embodiment, the cancer is pre-cancerous or pre-neoplastic.

In one embodiment, the cancer is a secondary cancer or metastases. The secondary cancer may be located in any organ or tissue, and particularly those organs or tissues having relatively higher hemodynamic pressures, such as lung, liver, kidney, pancreas, bowel and brain.

Other examples of cancer include blastoma (including medulloblastoma and retinoblastoma), sarcoma (including liposarcoma and synovial cell sarcoma), neuroendocrine tumors (including carcinoid tumors, gastrinoma, and islet cell cancer), mesothelioma, schwannoma (including acoustic neuroma), meningioma, adenocarcinoma, melanoma, leukemia or lymphoid malignancies, lung cancer including small-cell lung cancer (SGLG), non-small cell lung cancer (NSGLG), adenocarcinoma of the lung and squamous carcinoma of the lung, cancer of the peritoneum, hepatocellular cancer, gastric or stomach cancer including gastrointestinal cancer, pancreatic cancer, glioblastoma, ovarian cancer, liver cancer, bladder cancer, hepatoma, breast cancer (including metastatic breast cancer), cervical cancer, colon cancer, rectal cancer, colorectal cancer, salivary gland carcinoma, kidney or renal cancer, prostate cancer, thyroid cancer, hepatic carcinoma, anal carcinoma, penile carcinoma, testicular cancer, esophagael cancer, tumors of the biliary tract, as well as head and neck cancer.

"A condition or symptom associated" [with the cancer] may be any pathology that arises as a consequence of, preceding, or proceeding from the cancer. For example, where the cancer is a skin cancer, the condition or relevant symptom may be microbial infection. Where the cancer is a secondary tumor, the condition or symptom may relate to organ dysfunction of the relevant organ having tumor metastases. In one embodiment, the methods of treatment described herein are for the minimisation or treatment of a condition or symptom in an individual that is associated with a cancer in the individual.

In the above described embodiments, the formulation according to the invention may be useful for preventing doubling time of the cancer cells or otherwise inhibiting tumour growth, either through cytotoxic effect on the tumour cells or otherwise by generally inhibiting cell replication. In these embodiments it will be understood that the suppository formulation provides an anti neoplastic "monotherapy" effect.

In another embodiment, the method of treatment described above further includes the step of administering cytotoxic chemotherapy or radiotherapy to the individual.

In yet another embodiment there is provided a method of sensitising a cancer to chemo or radiotherapy including the steps of:
  providing an individual having a cancer in need of chemo or radiotherapy;
  administering to the individual a suppository, pessary or intra-urethral device formed from a formulation according to the invention;
  administering chemo or radio-therapy to the individual.

In another embodiment, the treatment provides for sensitisation of the tumour to radiotherapy, especially stereotactic radiotherapy. In one embodiment the treatment may provide for a reduction in tumour size utilising a sub-optimal radiation dose. It will be understood that a suboptimal radiation dose is one incapable of reducing tumour size in the absence of isoflavonoid formulation treatment.

In another embodiment, the treatment provides for sensitisation of the tumour to chemotherapy. In one embodiment, the treatment provides for a reduction in tumour size utilising a sub-optimal chemotherapy dose. It will be understood that a suboptimal chemotherapy dose is one incapable of reducing tumour size in the absence of isoflavonoid formulation treatment.

In one embodiment, the isoflavonoid formulation treatment is provided either as a cytotoxic monotherapy, or as a radio or chemosensitising therapy according to a variable dosing regime, prior to, or at the time of radio or chemotherapy. The variable dosing regime may include an increasing dose of isoflavonoid treatment during a run in period prior to radio or chemotherapy and/or an increasing dose during radio or chemotherapy. In one example, the isoflavonoid is provided in a dose of about 400 mg once daily for a period of 1 to 2 weeks and increased to 800 mg once daily for a period of 1 to 2 weeks or 1 month or longer, and further increased to 1600 mg (2×800 mg) once daily for a period of 1 to 2 weeks or 1 month or longer. Actual amounts will be influenced by disease status, age, weight, gender and other pharmacologically relevant variables.

In one particularly preferred embodiment, the cancer is primary or secondary prostate cancer, the isoflavonoid is idronoxil and the formulation is in the form of a suppository having a suppository base formed from, or consisting of Theobroma oil (cocoa butter). The idronoxil may be contained in the suppository in an amount of 400 mg or 800 mg. The idronoxil may be given once or twice daily for a period of 2 to 4 weeks, or for up to 12 months.

In one embodiment, the treatment provides for an inhibition of increase in prostate specific antigen (PSA) score, or for inhibition of tumour growth. In one embodiment the treatment provides for a reduction in PSA score, preferably a 50%, 60%, 70%, 80%, 90% or 100% reduction in PSA score.

It will be understood that the formulation may also be applied in the form of a device adapted for urethral application enabling the treatment of transitional epithelial carcinoma of the bladder.

It will be understood that the invention disclosed and defined in this specification extends to all alternative combinations of two or more of the individual features mentioned or evident from the text or drawings. All of these different combinations constitute various alternative aspects of the invention.

EXAMPLES

Example 1

Plasma Pharmacokinetic Studies of Idronoxil in Rats

1. Objective

The objective of this study in rodents is to determine the plasma pharmacokinetics of idronoxil after rectal delivery and intestinal delivery in lipids (cocoa butter or emulsion).

2. Study Design

Plasma Pharmacokinetic Studies Rats

Part (1); n=3 rats: Rectal administration of idronoxil in cocoa butter liquid formulation, collection of plasma.

Part (2); n=3 rats: Intestinal administration (intraduodenal infusion) of idronoxil in lipid formulation, collection of plasma.

Dosing Regimen:

3 mg idronoxil per rat (equivalent to 10 mg/kg idronoxil).

3. Formulation Preparation and Administration

Preparation of lipid formulation for intestinal dosing: Briefly, 3 mg of idronoxil, 80 mg oleic acid and 50 mg Tween 80 were mixed in a glass vial as the lipid phase. An aqueous phase consisting of 5.6 mL phosphate buffered saline (PBS, pH 7.4) was subsequently added to the lipid phase and the formulation emulsified by ultrasonication with a Misonix XL 2020 ultrasonic processor equipped with a 3.2-mm microprobe tip running at an amplitude of 240 μm and a frequency of 20 kHz for 4 min at room temperature.

Dose administration: The lipid formulations were infused into the duodenum of the rats at 2.8 mL/h for 2 h. After that, normal saline was infused into the duodenum at 2.8 mL/h for the remainder of the experiment to hydrate the animals.

Preparation of cocoa butter formulation for rectal dosing: Briefly, 100 mg of the cocoa butter was weighed into a homogenizer glass tube and melted at 32 degrees Celsius. 3 mg of idronoxil was then added and the formulation mixed manually with the homogenizer.

Dose administration: The warmed/melted cocoa butter formulations were dosed into the rectum via placing the tip of a 3 cm plastic mouse oral gavage device attached to a 1 ml plastic syringe exactly 1 cm into the rectum. The formulation was dosed over 15 sec. After that, normal saline was infused into the duodenum at 2.8 mL/h for the remainder of the experiment to hydrate the animals.

4. Surgical Procedure

Male Sprague-Dawley rats (n=3 per group, body weight 300±40 g) were used in the study. Each animal was fasted overnight prior to surgical cannulation of the carotid artery and duodenum.

The rats were anaesthetized (using isoflurane anesthesia), placed on a heated pad at 37° C. and cannulas were inserted into the duodenum (for dosing of lipid formulation and rehydration) and carotid artery (for blood collection).

Post-surgery, rats were re-hydrated for 0.5 h via intraduodenal infusion of normal saline at 2.8 mL/h prior to dosing via intraduodenal or rectal route.

5. Sample Collection and Data Analysis

Plasma collection: Plasma samples were collected for 8 h into Eppendorf tubes containing 5 μL of 1,000 IU/mL heparin. Aliquots (20 μL) of each hourly collected samples were transferred into labelled 1.5 mL Eppendorf tubes. Aliquoted and original bulk samples were stored at −20° C. until analysis.

Sample analysis: Plasma concentrations of idronoxil were measured by the HMST-lab using a validated HPLC-MS/MS method. Briefly, LC-MS analysis was performed on a Shimadzu 8050 triple quadrupole mass spectrometer coupled with a Shimadzu Nexera X2 UHPLC. MS analysis was conducted in positive mode electrospray ionisation and quantitation of the analytes performed in MRM mode. The column employed was a Phenomenex Kinetex EVO C18 column (2.6 μm particle size, 50×2.1 mm i.d.) equipped with a Phenomenex Security Guard column with C18 packing material. The column was maintained at 40-C. The mobile phase consisted of 0.2% formic acid in water (Mobile Phase A) and 100% acetonitrile (Mobile Phase B). Separations were conducted using a flow rate of 0.4 mL/min and an injection volume of 6 μL. Samples were controlled in the autosampler at a temperature of 10° C.

Non-compartmental pharmacokinetic (PK) analysis: The elimination rate constant (slope), half-life (i.e., 0.693/k), and mean residence time (MRT) were calculated using excel. The area under the plasma-concentration time curves from time zero to 8 h (AUC0-8 h) were calculated using the trapezoid rule to the last measured time point.

6. Results

Plasma concentrations of idronoxil over time following intestinal or rectal dosing to rats are shown in FIG. 1. FIG. 1 shows that rats receiving the idronoxil formulation rectally have a very different PK profile to rats that receive the formulation intestinally (note that intestinal delivery as per this study is an acceptable model of oral delivery), with 3 key differences.

The first difference is the considerably greater proportion of drug metabolized by Phase 2 metabolism in the intestinally-dosed rats than in the rectally-dosed rats (Table 2). Idronoxil Phase 2 metabolites have no anti-cancer activity, so that protection from Phase 2 metabolism is a desirable outcome with this drug. This points to a significant difference in the pharmacokinetics of idronoxil in the two dosage forms.

The second difference is that the maximum concentration of free idronoxil is significantly greater in the intestinally-dosed rats, although this is off-set by the third difference which is that the half-life of free idronoxil is considerably shorter in the intestinally-dosed rats. In these animals, the bulk of the total exposure is completed by about 3 hours from administration, whereas in the rectally-dosed rats, idronoxil levels readily achieve steady-state levels, remaining almost constant for at least 8 hours post administration. Critically, this latter exposure is at a concentration which in vitro studies suggest therapeutic efficacy.

In vitro studies have shown that idronoxil kills 50% of cancer cells in cell culture at a concentration of between about 200-1200 ng/mL, depending largely on the tumour type. The IC50 (Inhibitory Concentration that kills 50% of cells) is a standard method of comparing the cytotoxicity of compounds. Where the idronoxil is being used to sensitise cancer cells to the damaging effects of chemotherapy drugs and radiotherapy, the idronoxil is not required to kill the cancer cell, but to exert a non-lethal level of damage that renders it unable to resist the effects of other cytotoxic agents. This means that the concentration of idronoxil can be lowered to between about 50-300 ng/mL where it kills about 10% of the cancer cells.

Irrespective of whether the idronoxil is being used as a monotherapy or in combination with other anti-cancer agents, it is required to be present in the culture medium for most if not all the 48 hours it takes to kill the cancer cells. That is, adding the drug in a pulsatile manner to the cancer cell culture (left in for 2-3 hours and then removed), is largely ineffective to deliver either a direct cytotoxic effect or a sensitising effect. This concurs with the known mechanism of action of idronoxil which requires the ongoing presence of the drug to modify cell behaviour, rather than an acute poisoning effect. Thus, from a clinical perspective, it is more important to have the drug present on a continuous basis rather than on a pulsatile basis, with the requirement that it be present at a therapeutically effective level. On this basis, it is preferable to have idronoxil present in blood at a relatively steady-state level of between 20-400 ng/mL, with a preferred range of between 80-160 ng/mL.

In this study, idronoxil was given to rats at a dose of 10 mg/kg body weight, yielding a plasma concentration of about 35 to 40 ng/mL up to 8 hours from a single rectal administration. This dosage equates (on a body surface area basis) to a dose in humans of about 2 mg/kg BW. Thus, a blood level range of 20-400 ng/mL could be achieved in humans with a dosage range of 1-20 mg/kg BW, and the preferred range of 80-160 ng/mL with a dosage range of 4-8 mg/kg BW.

In this study, idronoxil dosed orally achieved blood levels >20 ng/mL for about 3 hours because of the short-half-life of the drug. To achieve blood levels on a relatively constant basis >20 ng/mL with oral dosing would mean repeat oral dosing every 3 hours, clearly a highly impractical and undesirable treatment regimen considering the need to treat with idronoxil over periods up to several weeks on a continuous basis.

In the case of rectal administration, depending on the required frequency of further rectal administrations, it is believed that idronoxil could be given at intervals not less than 18 hours, a highly practical dosing regimen.

7. Conclusions

Rectal and oral dosage delivery of idronoxil delivered approximately similar levels of 'free' (bio-active) idronoxil. However, oral delivery delivered the drug in this desirable form on a pulsatile basis, producing a higher $C_{max}$, but with a half-life of about 45 minutes that saw drug levels substantially fall within 2-3 hours and to be at sub-therapeutic levels before 4 hours. In contrast, rectal delivery maintained therapeutic levels of free idronoxil in the blood for at least 8 hours, and at the same time exposing the drug to a substantially lower level of Phase 2 metabolism. Given that the mechanism of action of idronoxil as a chemo-sensitiser or radio-sensitiser is dependent on a sustained presence of the drug in the blood, the rectal delivery of idronoxil obviates the need for repeat dosing, with repeat dosing being from 8 to 36 hours from a previous administration depending on the mg/kg dose of idronoxil given in the previous administration. This compares highly favourably with oral delivery where repeat dosings would be required every approximately 3-4 hours irrespective of whether a 5 to 20 mg/kg dose is given. This outcome with the rectal delivery is a highly desirable PK characteristic for idronoxil when used as a chemo- or radio-sensitiser.

TABLE 1

Plasma concentrations of idronoxil in rats

| Time Point (hr) | Idronoxil Plasma Concentration (ng/mL) | | | | |
|---|---|---|---|---|---|
| | Rat 1 | Rat 2 | Rat 3 | Mean | SD |
| Rectal delivery | | | | | |
| 0 | ND | ND | ND | 0.00 | |
| 1 | 26.69 | 96.45 | 24.95 | 49.36 | 40.79 |
| 2 | 15.89 | 88.10 | 24.70 | 42.90 | 39.40 |
| 3 | 15.93 | 74.16 | 21.77 | 37.29 | 32.06 |
| 4 | 14.41 | 53.69 | 22.34 | 30.14 | 20.78 |
| 5 | 27.95 | 71.42 | 39.54 | 46.30 | 22.51 |
| 6 | 17.77 | 51.34 | 21.62 | 30.24 | 18.37 |
| 7 | 20.60 | 42.95 | 11.44 | 25.00 | 16.21 |
| 8 | 5.74 | 33.39 | 16.06 | 18.40 | 13.97 |
| Intestinal delivery | | | | | |
| 0 | ND | 33.82 | ND | 33.82 | |
| 1 | 114.10 | 113.61 | 127.62 | 118.45 | 7.95 |
| 2 | 199.64 | 139.70 | 136.17 | 158.50 | 35.67 |
| 3 | 17.75 | 38.24 | 16.78 | 24.26 | 12.12 |
| 4 | 16.07 | 7.03 | 5.62 | 9.57 | 5.67 |
| 5 | 17.36 | 4.46 | 6.00 | 9.27 | 7.04 |
| 6 | 2.86 | 3.79 | 7.72 | 4.79 | 2.58 |
| 7 | 4.68 | 6.75 | 3.70 | 5.04 | 1.56 |
| 8 | 7.83 | 4.23 | 3.37 | 5.14 | 2.37 |

TABLE 2

Peak area of idronoxil and glucuronide metabolite in rat plasma following administration of formulation to rats

| Sampling Time | Peak Area | | | | | |
|---|---|---|---|---|---|---|
| | Rat 1 | | Rat 2 | | Rat 3 | |
| (hrs) | Idronoxil | Metabolite | Idronoxil | Metabolite | Idronoxil | Metabolite |
| Rectal administration | | | | | | |
| 0 | ND | ND | ND | ND | ND | ND |
| 1 | 57,590 | 158,795 | 213,825 | 311,254 | 46,167 | 218,034 |
| 2 | 37,493 | 189,840 | 179,554 | 483,638 | 50,847 | 349,843 |
| 3 | 37,603 | 199,483 | 152,537 | 497,307 | 45,812 | 422,680 |
| 4 | 34,050 | 172,091 | 117,814 | 573,493 | 49,738 | 415,899 |
| 5 | 61,323 | 160,881 | 153,360 | 556,779 | 75,786 | 467,819 |
| 6 | 41,246 | 152,651 | 114,191 | 714,318 | 42,370 | 403,326 |
| 7 | 46,844 | 145,022 | 100,506 | 640,052 | 25,104 | 333,633 |
| 8 | 14,934 | 117,384 | 80,236 | 620,559 | 40,752 | 387,424 |
| Intestinal administration | | | | | | |
| 0 | ND | ND | 62,126 | ND | ND | ND |
| 1 | 236,465 | 4,800,241 | 184,114 | 3,880,580 | 222,037 | 4,545,649 |
| 2 | 335,894 | 5,654,002 | 238,289 | 4,155,927 | 237,900 | 5,264,596 |
| 3 | 34,094 | 1,439,733 | 71,267 | 1,233,399 | 32,152 | 1,359,848 |
| 4 | 25,198 | 780,085 | 14,571 | 556,108 | 13,053 | 643,071 |
| 5 | 26,342 | 495,083 | 10,183 | 305,718 | 13,297 | 697,645 |
| 6 | 6,108 | 304,817 | 8,531 | 271,288 | 17,321 | 547,678 |
| 7 | 8,023 | 327,486 | 14,276 | 267,878 | 8,371 | 492,201 |
| 8 | 13,012 | 393,930 | 9,110 | 243,835 | 8,020 | 465,324 |

ND: not detected

The invention claimed is:

1. A method for providing in an individual requiring treatment for cancer, a steady state plasma concentration of a compound of Formula I of about 20 to 400 ng/mL, wherein:

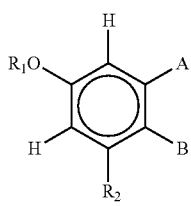

(I)

wherein $R_1$ is H, or $R_A CO$ where $R_A$ is $C_{1-10}$ alkyl or an amino acid;

$R_2$ is H, OH, or $R_B$ where $R_B$ is an amino acid or $COR_A$ where $R_A$ is as previously defined;

A and B together with the atoms between them form a six membered ring selected from the group

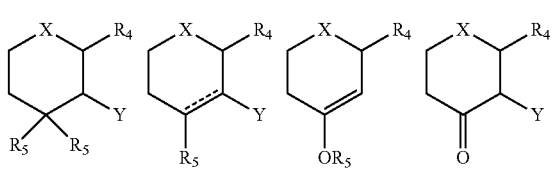

-continued

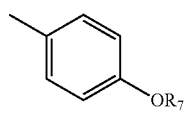

wherein $R_4$ is H, $COR_D$ where $R_D$ is H, OH, $C_{1-10}$ alkyl or an amino acid, $CO_2 R_C$ where $R_C$ is $C_{1-10}$ alkyl, $COR_E$ where $R_E$ is H, $C_{1-10}$ alkyl or an amino acid, COOH, $COR_C$ where $R_C$ is as previously defined, or $CONHR_E$ where $R_E$ is as previously defined;

$R_5$ is H, $CO_2 R_C$ where $R_C$ is as previously defined, or $COR_C OR_E$ where $R_C$ and $R_E$ are as previously defined, and where the two $R_5$ groups are attached to the same group they are the same or different;

$R_6$ is H, $CO_2 R_C$ where $R_C$ is as previously defined, $COR_C OR_E$ where $R_C$ and $R_E$ are as previously defined, substituted or unsubstituted aryl or substituted or unsubstituted heteroaryl;

X is O, N or S;

Y is where $R_7$ is H, or $C_{1-10}$ alkyl; and

" ===== " represents either a single bond or a double bond;

the method including the steps of:
a first rectal administration of a suppository formulation, the formulation including: a compound of Formula I in an amount of about 1 to 25 mg/kg body weight of the individual and a lipophilic suppository base;

further rectal administrations of the suppository formulation;

wherein each further rectal administration is no earlier than 8 hours after a previous rectal administration;

thereby providing in the individual a steady state plasma concentration of a compound of Formula I of about 20 to 400 ng/mL.

2. The method of claim 1 including providing a steady state plasma concentration of a compound of Formula I of about 80 to 160 ng/mL.

3. The method of claim 1 wherein the compound of Formula I is administered no earlier than 12 hours after a previous rectal administration.

4. The method of claim 1 wherein the compound of Formula I is administered no earlier than 24 hours after a previous rectal administration.

5. The method of claim 1 wherein the compound of Formula I is administered no earlier than 36 hours after a previous rectal administration.

6. The method of claim 1 wherein after the first rectal administration of the formulation to a patient there is provided in a plasma sample obtained from the patient at about 4 hours after the first administration of the formulation, a plasma concentration of compound of Formula I of about 20 to 400 ng/mL.

7. The method of claim 1 wherein there is provided in plasma samples obtained from the patient at 4 to 12 hours after the first administration of the formulation, a plasma concentration of compound of Formula I of about 20 to 400 ng/mL.

8. The method of claim 1, wherein the amount of the compound of Formula I provided in each administration is the same.

9. The method of claim 1, wherein each administration consists of the administration of a single suppository.

10. The method of claim 9, wherein the suppository contains 400 mg, 600 mg or 800 mg of the compound of Formula I.

11. The method of claim 1, wherein the individual is one who is receiving chemotherapy or radiotherapy for treatment of cancer and the steady state plasma concentration of the compound of Formula I potentiates a cytotoxic effect of the chemotherapy or radiotherapy.

12. The method of claim 1, wherein the steady state plasma concentration of the compound of Formula I is provided for the duration of the chemotherapy or radiotherapy treatment.

13. The method of claim 1, wherein the compound of Formula I is idronoxil.

14. The method of claim 13, wherein the idronoxil is at least partially dissolved in the lipophilic base.

15. The method of claim 14, wherein the lipophilic suppository base includes or consists of fatty acids.

16. The method of claim 15, wherein from 50 to 99% of the fatty acids are saturated fatty acids.

17. The method of claim 16, wherein 30 to 50% of fatty acids of the base are stearic acid, 20 to 30% of fatty acids of the base are palmitic acid, 15 to 25% of fatty acids of the base are lauric acid, 5 to 10% of fatty acids of the base are myristic acid.

18. The method of claim 1 wherein the compound of Formula I is administered about 12 hours after a previous rectal administration.

19. The method of claim 1 wherein the compound of Formula I is administered within 1 to 2 hours after 12 hours after a previous rectal administration.

20. The method of claim 1 wherein the compound of Formula I is administered about 8 to 12 hours after a previous rectal administration.

21. The method of claim 1 wherein the compound of Formula I is administered within 1 to 2 hours after 8 hours after a previous rectal administration.

22. The method of claim 1 wherein the compound of Formula I is administered about 8 hours after a previous rectal administration.

23. The method of claim 1 wherein the amount of the compound of Formula I provided in each administration is about 6 to 12 mg/kg body weight of the individual.

24. The method of claim 1, wherein the amount of the compound of Formula I provided in each administration is from 100 to 1600 mg.

25. The method of claim 1, wherein the amount of the compound of Formula I provided in each administration is about 1 to 5 mg/kg body weight of the individual.

26. The method of claim 1 wherein the amount of the compound of Formula I provided in each administration is about 12 to 25 mg/kg body weight of the individual.

* * * * *

UNITED STATES PATENT AND TRADEMARK OFFICE
CERTIFICATE OF CORRECTION

PATENT NO. : 11,559,510 B2  Page 1 of 1
APPLICATION NO. : 16/091716
DATED : January 24, 2023
INVENTOR(S) : Graham Kelly and Kate Porter It is certified that error appears in the above-identified patent and that said Letters Patent is hereby corrected as shown below:

In the Claims

In Claim 1, Column 33, Line 65, delete " 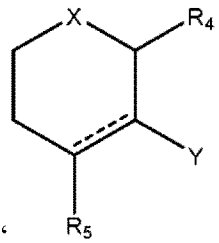 " and insert -- 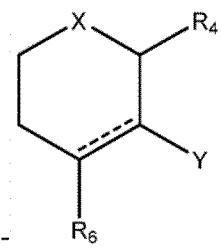 -- therefor.

Signed and Sealed this
Twenty-first Day of March, 2023

Katherine Kelly Vidal
*Director of the United States Patent and Trademark Office*